United States Patent

Nuebling et al.

Patent Number: 5,221,684
Date of Patent: Jun. 22, 1993

[54] HYDROQUINONE DIETHERS, COMPOUNDS WHICH ARE USEFUL FOR CONTROLLING PESTS

[75] Inventors: Christoph Nuebling, Hassloch; Hans Theobald, Limburgerhof; Wolfgang Krieg, Weingarten; Uwe Kardorff, Mannheim; Christoph Kuenast, Otterstadt, all of Fed. Rep. of Germany

[73] Assignee: BASF Aktiengesellschaft, Ludwigshafen, Fed. Rep. of Germany

[21] Appl. No.: 772,899

[22] Filed: Oct. 8, 1991

[30] Foreign Application Priority Data

Oct. 20, 1990 [DE] Fed. Rep. of Germany ....... 4033484

[51] Int. Cl.$^5$ .................. C07D 231/10; A01N 43/50
[52] U.S. Cl. .................................. 514/364; 514/359; 514/374; 514/378; 514/407; 548/100; 548/131; 548/132; 548/125; 548/215; 548/225; 548/226; 548/227; 548/228; 548/229; 548/235; 548/240; 548/243; 548/247; 548/144; 548/145; 548/365.7
[58] Field of Search ............... 548/144, 145, 100, 131, 548/132, 125, 215, 225, 226, 227, 228, 229, 235, 240, 243, 247, 374; 514/364, 359, 374, 378, 407

[56] References Cited

U.S. PATENT DOCUMENTS

| | | | |
|---|---|---|---|
| 4,943,585 | 7/1990 | Buerstinghaus et al. | 514/398 |
| 4,996,216 | 2/1991 | Leyendecker et al. | 514/338 |
| 5,071,860 | 12/1991 | Alig et al. | 514/332 |

FOREIGN PATENT DOCUMENTS

| | | | |
|---|---|---|---|
| 2010715 | 9/1990 | Canada | 548/342 |
| 0125315 | 11/1984 | European Pat. Off. | 514/338 |
| 2115812 | 9/1983 | United Kingdom | 564/325 |
| 2140010 | 11/1984 | United Kingdom | 546/339 |

*Primary Examiner*—C. Warren Ivy
*Assistant Examiner*—Zinna N. Davis
*Attorney, Agent, or Firm*—Keil & Weinkauf

[57] ABSTRACT

Hydroquinone diethers of the formula I

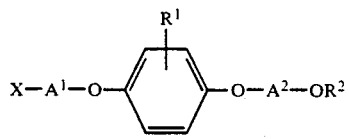

where
$A^1$ and $A^2$ are substituted or unsubstituted alkylene;
$R^1$ is hydrogen, halogen or alkyl;
$R^2$ is substituted or unsubstituted pyrazolyl or pyridyl;
X is a substituted or unsubstituted 5-membered heteroaromatic radical, are prepared as described using the described intermediates, and are used as pesticides.

4 Claims, No Drawings

HYDROQUINONE DIETHERS, COMPOUNDS WHICH ARE USEFUL FOR CONTROLLING PESTS

The present invention relates to hydroquinone diethers of the formula I

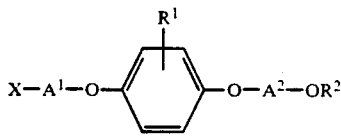

where
A$^1$ is methylene, ethylene or propylene, each of which can carry one or two C$_1$-C$_3$-alkyl radicals;
A$^2$ is ethylene or propylene, each of which can carry one or two C$_1$-C$_3$-alkyl radicals;
R$^1$ is hydrogen, halogen or C$_1$-C$_6$-alkyl;
R$^2$ is 1-pyrazolyl which can carry one to three of the following: halogen and C$_1$-C$_3$-alkyl, or 2-, 3- or 4-pyridyl which can carry one to three of the following: cyano, nitro, halogen, C$_1$-C$_3$-alkyl, C$_1$-C$_2$-haloalkyl, C$_1$-C$_3$-alkoxy, C$_1$-C$_2$-haloalkoxy, C$_1$-C$_3$-alkylthio, C$_1$-C$_3$-alkoxy-C$_1$-C$_3$-alkyl or C$_3$-C$_6$-cycloalkyl;
X is a five-membered heteroaromatic radical which contains one to three nitrogen atoms and/or one oxygen or sulfur atom as hetero atoms, and which can carry one to three of the following: nitro, halogen, C$_1$-C$_6$-alkyl, C$_1$-C$_4$-haloalkyl, C$_1$-C$_6$-alkoxy, C$_1$-C$_4$-haloalkoxy, C$_1$-C$_4$-alkylthio, C$_1$-C$_4$-haloalkylthio, C$_1$-C$_3$-alkoxy-C$_1$-C$_4$-alkyl, C$_3$-C$_8$-cycloalkyl, C$_2$-C$_8$-alkenyl, aryl or aryl-C$_1$-C$_{10}$-alkyl, where the aromatic radicals in turn can carry one to five halogen atoms and/or one to three of the following: C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio or C$_1$-C$_4$-haloalkylthio.

The present invention also relates to processes for preparing these compounds, to pesticides containing them and to methods for controlling pests.

The present invention furthermore relates to intermediates for preparing the hydroquinone diethers I, namely diethers of the formula IV

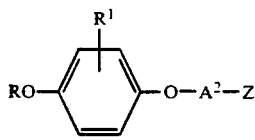

where
A$^2$ and R$^1$ have the abovementioned meanings, and
R is C$_1$-C$_6$-alkyl; benzyl which can carry on the aromatic radical one to five halogen atoms and/or one to three of the following: cyano, nitro, C$_1$-C$_4$-alkyl, C$_1$-C$_4$-alkoxy or C$_1$-C$_4$-alkylthio; silyl which carries three of the following: C$_1$-C$_6$-alkyl and/or phenyl which can carry one to five halogen atoms and/or one to three of the following: cyano, nitro, C$_1$-C$_4$-alkyl, C$_1$-C$_4$-alkoxy or C$_1$-C$_4$-alkylthio;
Z is hydroxyl; halogen; C$_1$-C$_{10}$-alkylsulfonyl, phenylsulfonyl which can carry on the aromatic radical one to five halogen atoms and/or one to three of the following: cyano, nitro, C$_1$-C$_4$-alkyl, C$_1$-C$_4$-alkoxy or C$_1$-C$_4$-alkylthio; 1-pyrazolyloxy which can carry one to three of the following: halogen and C$_1$-C$_3$-alkyl, or 2-, 3- or 4-pyridyloxy which can carry one to three of the following: cyano, nitro, halogen, C$_1$-C$_3$-alkyl, C$_1$-C$_2$-haloalkyl, C$_1$-C$_3$-alkoxy, C$_1$-C$_2$-haloalkoxy, C$_1$-C$_3$-alkylthio, C$_1$-C$_3$-alkoxy-C$_1$-C$_3$-alkyl or C$_3$-C$_6$-cycloalkyl, and monoethers of the formula VI

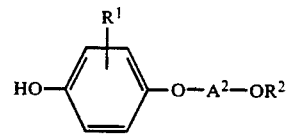

where A$^2$, R$^1$ and R$^2$ have the meanings given above.

Hydroquinone diethers with a pesticidal action are disclosed in the literature (phenoxyphenoxyalkyl O-oxime ethers: GB TM A 21 15 812; phenoxyphenoxyalkylpyrazoles: EP-A 289 919; phenoxyphenoxyalkyl hetaryl ethers: GB-A 21 40 010; phenoxyphenoxyalkyl N-pyrazolyl and N-triazolyl ethers: DE-A 39 06 772 and DE-A 39 41 296 (O.Z. 40623)) but their action against pests is not always satisfactory, for example at low application rates.

It is an object of the present invention to provide novel compounds suitable for controlling pests and processes for the preparation thereof and the use thereof.

We have found that this object is achieved by the hydroquinone diethers I defined in the first paragraph. We have also found processes and novel intermediates for preparing these hydroquinone diethers, pesticides containing them and processes for the use thereof.

The hydroquinone diethers I can be obtained in a variety of ways.

They are particularly advantageously obtained in a conventional manner by reacting a hydroquinone monoether II in an inert organic solvent in the presence of a base with an ethylene or propylene derivative III to give a diether IVa, then reacting IVa with a hydroxyl compound V, converting the resulting diether IVb by eliminating the protective group R into the corresponding monoether VI, and then reacting the latter with an arylalkyl compound VII to give I.

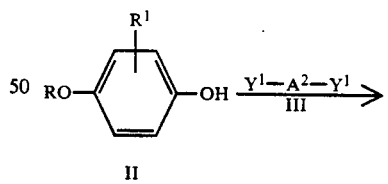

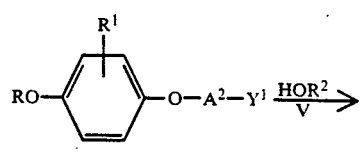

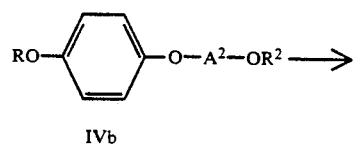

-continued

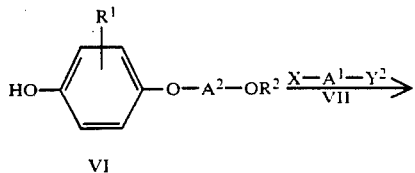

VI

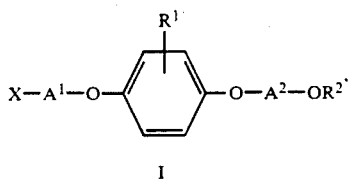

I

R in the formulae II, IVa and IVb is an inert protective group such as $C_1$-$C_6$-alkyl, especially 1,1-dimethylethyl, benzyl which is unsubstituted or substituted in the phenyl moiety, especially benzyl, 4-methylbenzyl and 2,4,6-trimethylbenzyl, silyl which is trisubstituted by organic radicals bonded via carbon, preferably trimethylsilyl, tert-butyldimethylsilyl, phenyldimethylsilyl and tert-butyldiphenylsilyl, especially tert-butyldimethylsilyl, $C_1$-$C_4$-alkoxy-$C_1$-$C_2$-alkyl such as methoxymethyl, ethoxymethyl, 1-methoxyethyl and 1-ethoxyethyl, especially methoxymethyl or methoxyethoxymethyl.

$Y^1$ and $Y^2$ in the formulae III, IVa and VII are each nucleofugic leaving groups, for example halogen such as fluorine, chlorine, bromine and iodine, preferably chlorine, bromine and iodine, especially chlorine and bromine, sulfonyl substituted by organic radicals bonded via carbon, especially methylsulfonyl, trifluoromethylsulfonyl, phenylsulfonyl, 4-tolylsulfonyl and 2,4,6-trimethylphenylsulfonyl or $C_1$-$C_4$-alkylcarbonyloxy such as methylcarbonyloxy (acetyl), ethylcarbonyloxy (propionyl), 1-methylethylcarbonyloxy, which can carry one to five fluorine atoms, for example trifluoromethylcarbonyloxy (trifluoroacetyl), benzoyl which can carry one to three halogen atoms such as fluorine, chlorine and bromine and/or nitro groups.

The reaction of compounds II with III, IVa with V and VI with VII are each etherifications and are carried out by conventional methods for this (Houben-Weyl, Vol. VI/3, pp. 1 ff., 49 ff. (1965)).

The etherification is normally carried out at from −50° to 150° C., preferably from −20° to 120 C.

The etherification generally takes place at an adequate rate above −20° C. It is not usually necessary to exceed 120° C. for complete conversion. The reaction may evolve heat, which may make it advantageous to provide means of cooling.

Suitable bases are, in general, inorganic compounds such as alkali metal and alkaline earth metal hydroxides, for example lithium hydroxide, sodium hydroxide, potassium hydroxide and calcium hydroxide, alkali metal and alkaline earth metal oxides, for example lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates, for example lithium carbonate and calcium carbonate, alkali metal bicarbonates, for example sodium bicarbonate, organometallic compounds, especially alkali metal alkyls, for example methyllithium, butyllithium and phenyllithium, alkali metal and alkaline earth metal alcoholates, for example sodium methanolate, sodium ethanolate, potassium ethanolate, potassium tertbutanolate and dimethoxymagnesium, also organic bases, e.g. tertiary amines such as trimethylamine, triethylamine, diisopropylethylamine and n-methylpiperidine, pyridine, substituted pyridines such as collidine, lutidine and 4-dimethylaminopyridine, and bicyclic amines. Potassium hydroxide, potassium carbonate, sodium methylate, sodium ethylate, potassium tert-butylate and sodium hydride are particularly preferred. Normally at least equivalent amounts of the base are used, but the latter can also be used in excess or, where appropriate, as solvent.

Examples of suitable solvents are aliphatic hydrocarbons such as pentane, hexane, cyclohexane and petroleum ether, aromatic hydrocarbons such as toluene, o-, m- and p-xylenes, halohydrocarbons such as methylene chloride, ethylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol and isopropanol, and aprotic dipolar solvents such as dimethyl sulfoxide, dimethylformamide and pyridine, particularly preferably acetonitrile, ethanol and dimethylformamide.

It is also possible to use mixtures of the said solvents.

The starting materials are usually reacted together in stoichiometric amounts. It may be advantageous, for example to increase the yield, to use one of the starting materials in an excess of from 0.1 to 10 mole equivalents, preferably 0.2 to 1.5 mole equivalents.

Where $Y^1$ or $Y^2$ in one of the formulae III, IVa or VII is chlorine or bromine, the reaction rate can generally be increased by adding catalytic amounts of potassium iodide. The catalyst is normally used in amounts of from 5 to 20 mol %.

The elimination of the protective group R from the compound IVb is likewise carried out in a conventional manner in a solvent in the presence of an acid or of an acidic catalyst (Houben-Weyl, vol. VI/1c, pp. 314 ff (1976)).

The ethers IVb are generally cleaved at from −20° C. to 120° C., preferably 20° C. to 100° C.

Solvents suitable for the cleavage are those mentioned above for the etherification, especially methanol, ethanol, chloroform and dioxane and mixtures thereof.

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, as well as organic acids such as formic acid, acetic acid, propionic acid, oxalic acid, citric acid and trifluoroacetic acid. The acids are generally employed in catalytic amounts, but they can also be used in equimolar amounts, in excess or, where appropriate, as solvent.

Besides the preparation method described above, the diethers IVa are also obtained by reacting a hydroquinone monoether II in a conventional manner (U.S. Pat. No. 4,310,706) in an inert organic solvent in the presence of a base with a cyclic carbonate VIII, and halogenating or sulfonylating the resulting diether alcohol IV (Z=hydroxyl).

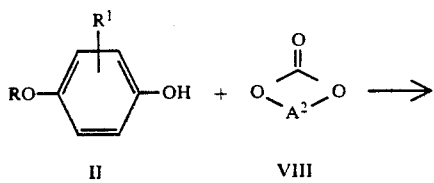

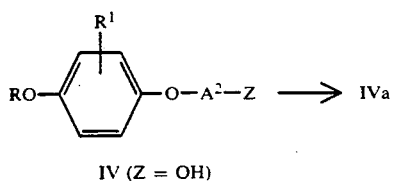

IV (Z = OH)

The diethers IVb where $R^2$ is 2-, 3- or 4-pyridyl are advantageously obtained from the diether alcohols IV (Z=hydroxyl) by subjecting the latter to a nucleophilic substitution with an appropriate halogenated pyridine derivative IX (Houben-Weyl, vol. V/4, pp. 710 ff. (1960)).

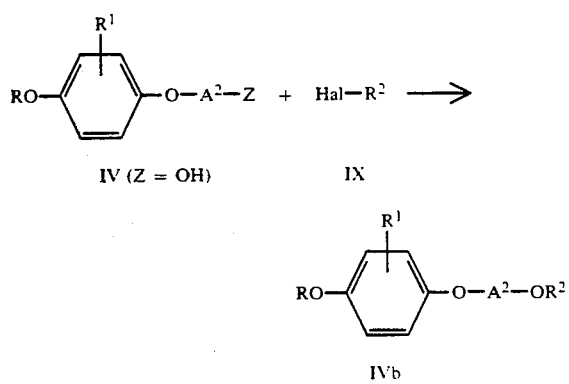

In this connection, $R^2$ is, in particular, a pyridine derivative which has a halogen atom (Hal) such as fluorine, chlorine or bromine in position 2, 3 or 4. The reaction is carried out under conditions similar to those described for the reaction of II with III, IVa with V and VI with VII.

The reaction mixtures are worked up in a conventional manner, e.g. by mixing with water, separating the phases and, where appropriate, purifying the crude products by chromatography. The intermediates and final products are in some cases obtained in the form of colorless or pale brown viscous oils which are purified or freed of volatiles under reduced pressure and at moderately elevated temperature. Where the intermediates and final products are obtained as solids, they can be purified by recrystallization or digestion.

The hetarylalkyl derivatives of the formula VII required for the reaction are either known, commercially available or can be prepared by conventional chemical processes.

Processes for preparing thiophene derivatives are to be found, for example, in: Comprehensive Heterocyclic Chemistry, A. R. Katritzky and C. W. Rees, Vol. 4, pp. 863 ff., Pergamon Press 1984; thiazole, oxazole, isothiazole, thiadiazole and oxadiazole derivatives for example in: Comprehensive Heterocyclic Chemistry, A. R. Katritzky and C. W. Rees, Vol. 6, pp. 131, 177, 235, 365, 427, 545 ff., Pergamon Press 1984; imidazole derivatives for example in: Advances in Heterocyclic Chemistry, Vol. 27, pp. 242 ff., 1980; pyrazole and triazole derivatives for example in Comprehensive Heterocyclic Chemistry, A. R. Katritzky and C. W. Rees, Vol. 5, pp. 167, 733 ff., Pergamon Press 1984; isoxazole derivatives for example in DE-A 25 49 962 and DE-A 27 54 832.

N-Methylazoles are either disclosed in Heterocycles 24 (1986) 2233-2237 or can be prepared by the method described therein by reacting the azoles with paraformaldehyde.

With a view to the intended use of the compounds I in pesticides, radicals suitable as substituents are the following:

$A^1$ methylene, ethylene or propylene, preferably methylene and ethylene; especially methylene, it being possible for these groups to carry one or two $C_1-C_3$-alkyl radicals such as methyl, ethyl, propyl and 1-methylethyl, preferably methyl and ethyl, especially methyl;

$A^2$ ethylene or propylene, it being possible for these groups to carry one or two $C_1-C_3$-alkyl radicals such as methyl, ethyl, propyl and 1-methylethyl; preferably methyl and ethyl, especially methyl;

$R^1$ hydrogen, halogen such as fluorine, chlorine, bromine and iodine, preferably fluorine, chlorine and bromine, especially fluorine and chlorine, or $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_1-C_3$-alkyl, especially methyl;

$R^2$ 1-pyrazolyl which can carry one to three of the following:

halogen such as fluorine, chlorine, bromine and iodine, preferably fluorine, chlorine and bromine, especially fluorine and chlorine, and $C_1-C_3$-alkyl such as methyl, ethyl, propyl and 1-methylethyl, preferably methyl and ethyl, especially methyl, or 2-, 3- or 4-pyridyl which can carry one to three of the following: cyano, nitro, halogen such as fluorine, chlorine, bromine and iodine, preferably fluorine, chlorine and bromine, especially fluorine and chlorine, $C_1-C_3$-alkyl such as methyl, ethyl, propyl and 1-methylethyl, preferably methyl and ethyl, especially methyl; $C_1-C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably $C_1$-haloalkyl, especially trifluoromethyl;

$C_1-C_3$-alkoxy such as methoxy, ethoxy, propoxy and 1-methylethoxy, preferably $C_1-C_2$-alkoxy, especially methoxy;

$C_1$–$C_2$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chlorofluoroethoxy, 2-chloro-2,2-difluoroethoxy, 2,2-dichloro-2-fluoroethoxy, 2,2,2-trichloroethoxy and pentafluoroethoxy, preferably $C_1$-haloalkoxy, especially trifluoromethoxy;

$C_1$–$C_3$-alkylthio such as methylthio, ethylthio, propylthio and 1-methylethylthio, preferably $C_1$–$C_2$-alkylthio, especially methylthio;

$C_1$–$C_3$-alkoxy-$C_1$–$C_3$-alkyl such as methoxymethyl, ethoxymethyl, propoxymethyl, 1-methylethoxymethyl, 1-methoxyethyl, 1-ethoxyethyl, 1-propoxyethyl, 1-methyl-1-ethoxyethyl, 2-methoxyethyl, 2-ethoxyethyl, 2-propoxyethyl, 1-methyl-2-ethoxyethyl, 1-methoxypropyl, 1-ethoxypropyl, 1-propoxypropyl, 1-isopropoxypropyl, 1-methoxy-2-propyl, 1-ethoxy-2-propyl, 1-propoxy-2-propyl, 1-isopropoxy-2-propyl, 3-methoxypropyl, 3-ethoxypropyl, 3-propoxypropyl, 3-isopropoxypropyl, preferably $C_1$–$C_2$-alkoxy-$C_1$–$C_2$-alkyl, especially methoxymethyl, ethoxymethyl and 1-methoxyethyl, or $C_3$–$C_6$-cycloalkyl such as cyclopropyl, cyclobutyl, cyclopentyl and cyclohexyl, preferably cyclopropyl, cyclopentyl and cyclohexyl, especially cyclopropyl;

X a five-membered heteroaromatic radical containing one to three nitrogen atoms and/or one oxygen or sulfur atom as hetero atoms, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, preferably a heteroaromatic radical containing one or two nitrogen atoms or one or two nitrogen atoms and one oxygen or one sulfur atom, especially 1-imidazolyl, 3-isoxazolyl, 5-isoxazolyl, 1,3,4-oxadiazol-2-yl and 1,3,4-thiadiazol-2-yl, which can carry one to three of the following: nitro, halogen such as fluorine, chlorine, bromine and iodine, preferably fluorine, chlorine and bromine, especially fluorine and chlorine, $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_1$–$C_4$-alkyl, especially methyl, ethyl and propyl;

$C_1$–$C_4$-haloalkyl, especially $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably $C_1$-haloalkyl, especially trifluoromethyl;

$C_1$–$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably $C_1$–$C_3$-alkoxy, especially methoxy and ethoxy;

$C_1$–$C_4$-haloalkoxy, especially $C_1$–$C_2$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy,2-chloro-2-fluoroethoxy,2-chloro-2,2-difluoroethoxy, 2,2-dichloro-2-fluoroethoxy, 2,2,2-trichloroethoxy and pentafluoroethoxy, preferably $C_1$-haloalkoxy, especially trifluoromethoxy and difluoromethoxy;

$C_1$–$C_4$-alkylthio such as methylthio, ethylthio, propylthio, 1-methylethylthio, butylthio, 1-methylpropylthio, 2-methylpropylthio and 1,1-dimethylethylthio, preferably $C_1$–$C_2$-alkylthio, especially methylthio;

$C_1$–$C_4$-haloalkylthio, especially $C_1$–$C_2$-haloalkylthio, such as chloromethylthio, dichloromethylthio, trichloromethylthio, fluoromethylthio, difluoromethylthio, trifluoromethylthio, chlorofluoromethylthio,dichlorofluoromethyl-thio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio, preferably $C_1$-haloalkylthio, especially trifluoromethylthio;

$C_1$–$C_3$-alkoxy-$C_1$–$C_4$-alkyl, especially $C_1$–$C_3$-alkoxy-$C_1$–$C_3$-alkyl such as methoxymethyl, ethoxymethyl, propoxymethyl, 1-methylethoxymethyl, methoxy-1-ethyl, ethoxy-1-ethyl, propoxy-1-ethyl, 1-methylethoxy-1-ethyl,methoxy-2-ethyl, ethoxy-2-ethyl, propoxy-2-ethyl, 1-methylethoxy-2-ethyl, methoxy-1-propyl, ethoxy-1-propyl, propoxy-1-propyl, 1-methylethoxy-1-propyl, methoxy-2-propyl, ethoxy-2-propyl, propoxy-2-propyl, 1-methylethoxy-2-propyl, methoxy-3-propyl, ethoxy-3-propyl, propoxy-3-propyl, 1-methylethoxy-3-propyl, preferably $C_1$–$C_2$-alkoxy-$C_1$–$C_2$-alkyl, especially methoxymethyl, ethoxymethyl and 1-methoxyethyl;

$C_3$–$C_8$-cycloalkyl such as cyclopropyl, cyclobutyl, cyclopentyl, cyclohexyl, cycloheptyl and cyclooctyl, preferably cyclopropyl, cyclopentyl and cyclohexyl, especially cyclopropyl;

$C_2$–$C_8$-alkenyl, especially $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, preferably $C_2C_4$-alkenyl, especially ethenyl, 1-propenyl and 2-propenyl;

aryl such as phenyl, 1-naphthyl and 2-naphthyl, preferably phenyl, or $C_1$–$C_{10}$-alkyl which is substituted by aryl as mentioned above, especially $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_1$–$C_4$-alkyl, especially methyl, ethyl and propyl, where the aromatic radicals in turn can carry one to five halogen atoms such as fluorine, chlorine, bromine and iodine, preferably fluorine, chlorine and bromine, especially fluorine and chlorine, and/or one to three of the following:

$C_1$–$C_4$-alkyl such as methyl, ethyl, propyl, 1-methylethyl, butyl, 1-methylpropyl, 2-methylpropyl and 1,1-dimethylethyl, preferably $C_1$–$C_3$-alkyl, especially methyl and ethyl;

$C_1$–$C_4$-haloalkyl, especially $C_1$–$C_2$-haloalkyl such as chloromethyl, dichloromethyl, trichloromethyl, fluoromethyl, dichlorofluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably $C_1$-haloalkyl, especially trifluoromethyl;

$C_1$–$C_4$-alkoxy such as methoxy, ethoxy, propoxy, 1-methylethoxy, butoxy, 1-methylpropoxy, 2-methylpropoxy and 1,1-dimethylethoxy, preferably methoxy, ethoxy and propoxy, especially methoxy and ethoxy;

$C_1$–$C_4$-haloalkoxy, especially $C_1$–$C_2$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy,2-chloro-2-fluoroethoxy,2-chloro-2,2-difluoroethoxy, 2,2-dichloro-2-fluoroethoxy, 2,2,2-trichloroethoxy and pentafluoroethoxy, preferably $C_1$-haloalkoxy, especially difluoromethoxy and trifluoro-$C_1$–$C_4$-alkylthio such as methylthio, ethylthio, propylthio, 1-methylethylthio, butylthio, 1-methylpropylthio, 2-methylpropylthio and 1,1-dimethylethylthio, preferably $C_1$–$C_2$-alkylthio, especially methylthio; or $C_1$–$C_4$-haloalkylthio, especially $C_1$–$C_2$-haloalkylthio such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio, preferably $C_1$-haloalkylthio, especially trifluoromethylthio.

Particularly preferred 5-membered heteroaromatic substituents X are listed below, where the possible substituents are not indicated for clarity; the bond to $A^1$ is indicated by .- .

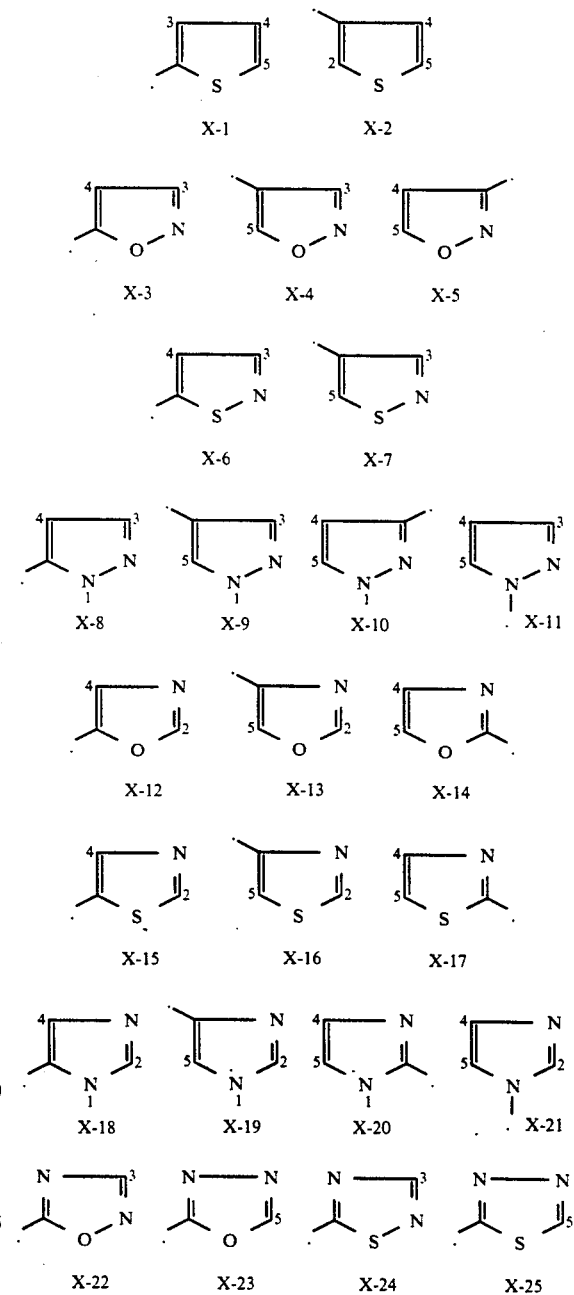

-continued

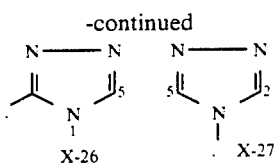

-continued

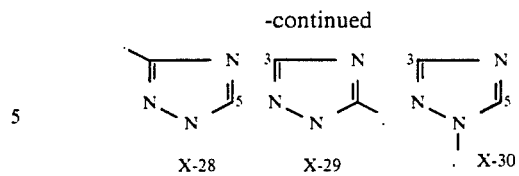

Examples of particularly preferred compounds of the formula I are listed in Tables A and B which follow.

TABLE A $$X-A^1-O-\underset{2\ 3}{\bigcirc}-O-A^2-O-N=\underset{}{\overset{N}{\bigg\langle}}-R'_n \quad IA$$

with $R^1$ on the phenyl ring

| x | Substituent on x | $A^1$ | $R^1$ | $A^2$ | $R'_n$ |
|---|---|---|---|---|---|
| x-1 | — | $CH_2$ | H | $CH_2CH_2$ | H |
| x-1 | — | $CH(CH_3)$ | H | $CH_2CH_2$ | H |
| x-1 | — | $CH(CH_2CH_3)$ | H | $CH_2CH_2$ | H |
| x-1 | — | $CH_2$ | 3-F | $CH_2CH_2$ | H |
| x-1 | — | $CH_2CH_2$ | H | $CH_2CH_2$ | H |
| x-1 | — | $CH_2$ | H | $CH(CH_3)CH_2$ | H |
| x-1 | — | $CH_2$ | H | $CH_2CH(CH_3)$ | H |
| x-1 | — | $CH_2$ | H | $CH_2CH_2CH_2$ | H |
| x-1 | 5-$CH_3$ | $CH_2$ | H | $CH_2CH_2$ | H |
| x-1 | 4-$CH_3$ | $CH_2$ | H | $CH_2CH_2$ | H |
| x-1 | 3-$CH_3$ | $CH_2$ | H | $CH_2CH_2$ | H |
| x-1 | 5-Cl | $CH_2$ | H | $CH_2CH_2$ | H |
| x-1 | 5-Br | $CH_2$ | H | $CH_2CH_2$ | H |
| x-1 | 4-Cl | $CH_2$ | H | $CH_2CH_2$ | H |
| x-1 | 4-Br | $CH_2$ | H | $CH_2CH_2$ | H |
| x-1 | 5-Cyclopropyl | $CH_2$ | H | $CH_2CH_2$ | H |
| x-1 | 4-Cyclopropyl | $CH_2$ | H | $CH_2CH_2$ | H |
| x-1 | 4,5-Dichloro | $CH_2$ | H | $CH_2CH_2$ | H |
| x-1 | 5-Br | $CH_2$ | H | $CH_2CH_2$ | 4-Cl |
| x-1 | 5-Br | $CH_2$ | H | $CH_2CH_2$ | 3,5-$(CH_3)_2$ |
| x-1 | 4,5-Dichloro | $CH_2$ | 3-F | $CH(CH_3)CH_2$ | 4-Cl |
| x-1 | 5-$CH_3$ | $CH_2$ | H | $CH_2CH(CH_3)$ | 3,5-$(CH_3)_2$ |
| x-1 | 5-Br | $CH_2$ | H | $CH_2CH_2CH_2$ | 4-Cl |
| x-2 | — | $CH_2$ | H | $CH_2CH_2$ | H |
| x-2 | 4-Cyclopropyl | $CH_2$ | H | $CH_2CH_2$ | H |
| x-2 | 5-Cyclopropyl | $CH(CH_3)$ | H | $CH(CH_3)CH_2$ | H |
| x-2 | 4-Cl | $CH_2$ | H | $CH_2CH(CH_3)$ | H |
| x-2 | 5-Br | $CH_2$ | H | $CH_2CH_2$ | H |
| x-2 | 4,5-Dichloro | $CH_2CH_2$ | H | $CH_2CH_2CH_2$ | H |
| x-2 | 4,5-Dibromo | $CH_2$ | 3-F | $CH_2CH_2$ | H |
| x-2 | 5-Br | $CH(CH_2CH_3)$ | H | $CH_2CH_2$ | 3,5-$(CH_3)_2$ |
| x-2 | 5-Br | $CH_2$ | H | $CH_2CH(CH_3)$ | 4-Cl |
| x-2 | 4-Cl | $CH_2$ | 3-F | $CH(CH_3)CH(CH_3)$ | 4-Cl |
| x-2 | 5-Cyclopropyl | $CH_2$ | H | $CH_2CH(CH_3)$ | 3,5-$(CH_3)_2$ |
| x-2 | 4-Cyclopropyl | $CH_2CH_2$ | H | $CH_2CH_2CH_2$ | H |
| x-3 | 3-$CH_3$ | $CH_2$ | H | $CH_2CH_2$ | H |
| x-3 | 3-$CH_2CH_3$ | $CH_2$ | H | $CH_2CH_2$ | H |
| x-3 | 3-$CH(CH_3)_2$ | $CH_2$ | H | $CH_2CH_2$ | H |
| x-3 | 3-Cyclopropyl | $CH_2$ | H | $CH_2CH_2$ | H |
| x-3 | 3-$OCH_2CH_3$ | $CH_2$ | H | $CH_2CH_2$ | H |
| x-3 | 3-$CH_2OCH_3$ | $CH_2$ | H | $CH_2CH_2$ | H |
| x-3 | 3-$CF_3$ | $CH_2$ | H | $CH_2CH_2$ | H |
| x-3 | 3-$CH_3$ | $CH_2$ | H | $CH_2CH_2$ | 4-Cl |
| x-3 | 3-Cyclopropyl | $CH_2$ | H | $CH_2CH_2$ | 4-Cl |
| x-3 | 3-$CH(CH_3)_2$ | $CH_2$ | H | $CH_2CH(CH_3)$ | 3,5-$(CH_3)_2$ |
| x-3 | 3-$CH_3$ | $CH_2$ | H | $CH(CH_3)CH_2CH_2$ | H |
| x-3 | 3-Cyclopropyl | $CH_2CH_2CH_2$ | H | $CH_2CH_2$ | 4-Cl |
| x-3 | 3-$CF_3$ | $CH_2CH_2$ | 3-F | $CH_2CH_2$ | H |
| x-3 | 3-$OCH_2CH_3$ | $CH(CH_3)$ | H | $CH(CH_3)CH(CH_3)$ | H |
| x-3 | 3-$CH_2CH_3$ | $CH_2$ | 3-$CH_3$ | $CH_2CH_2$ | 3,5-$(CH_3)_2$ |
| x-4 | — | $CH_2$ | H | $CH_2CH_2$ | H |
| x-4 | 5-$CH_3$ | $CH_2$ | H | $CH_2CH(CH_3)$ | H |
| x-4 | 3-$CH_3$ | $CH_2$ | H | $CH_2CH(CH_3)$ | H |
| x-4 | 3-$CH(CH_3)_2$ | $CH_2$ | H | $CH_2CH_2$ | 4-Cl |
| x-4 | 3-$OCH_2CH_3$ | $CH(CH_3)$ | H | $CH(CH_3)CH_2$ | 3,5-$(CH_3)_2$ |
| x-4 | 5-$OCH_2CH_3$ | $CH_2$ | 3-F | $CH(CH_3)CH(CH_3)$ | H |
| x-4 | 5-$CH(CH_3)_2$ | $CH_2CH_2$ | H | $CH_2CH_2CH(CH_3)$ | H |
| x-5 | — | $CH_2$ | H | $CH_2CH_2$ | H |
| x-5 | 5-$CH_3$ | $CH_2$ | H | $CH_2CH_2$ | H |
| x-5 | 5-Cyclopropyl | $CH_2$ | H | $CH_2CH_2$ | H |

TABLE A-continued

IA

| x | Substituent on x | A¹ | R¹ | A² | R'ₙ |
|---|---|---|---|---|---|
| x-5 | 5-OCH₂CH₃ | CH₂CH₂ | H | CH₂CH(CH₃) | 4-Cl |
| x-5 | 5-Cyclopropyl | CH(CH₃) | H | CH₂CH(CH₃) | 3,5-(CH₃)₂ |
| x-5 | 5-Cyclopropyl | CH₂ | H | CH(CH₃)CH₂ | H |
| x-5 | 5-CH₃ | CH(CH₃) | 3-F | CH₂CH₂ | 4-Cl |
| x-5 | 5-CH₃ | CH₂CH₂CH₂ | H | CH₂CH₂CH₂ | H |
| x-5 | 5-OCH₂CH₃ | CH₂ | H | CH₂CH(CH₃) | 3,5-(CH₃)₂ |
| x-6 | — | CH₂ | 3-F | CH₂CH₂ | H |
| x-6 | 3-CH₃ | CH₂ | H | CH₂CH₂ | H |
| x-6 | 3-Cyclopropyl | CH₂ | H | CH₂CH₂ | H |
| x-6 | 3-OCH₂CH₃ | CH₂ | H | CH₂CH₂ | H |
| x-6 | 3-Cyclopropyl | CH(CH₃) | H | CH(CH₃)CH₂ | 4-Cl |
| x-6 | 3-Cyclopropyl | CH₂CH₂ | H | CH₂CH₂CH₂ | H |
| x-6 | 3-CH₃ | CH₂ | H | CH₂CH(CH₃) | 4-Cl |
| x-6 | 3-CH₃ | CH₂ | 3-CH₃ | CH₂CH(CH₃) | 3,5-(CH₃)₂ |
| x-6 | 3-Cyclopropyl | CH₂ | H | CH(CH₃)CH(CH₃) | H |
| x-7 | — | CH₂ | H | CH₂CH₂ | H |
| x-7 | 3-CH₃ | CH₂ | H | CH₂CH₂ | H |
| x-7 | 3-CH₃ | CH₂ | 3-CH₃ | CH(CH₃)CH₂ | H |
| x-7 | 3-CH₃ | CH₂ | H | CH(CH₃)CH₂ | H |
| x-7 | 3-CH₃ | CH(CH₃) | H | CH₂CH(CH₃) | 4-Cl |
| x-7 | 3-CH₃ | CH₂ | H | CH₂CH(CH₃) | 3,5-(CH₃)₂ |
| x-8 | 1-CH₃ | CH₂ | H | CH₂CH₂ | H |
| x-8 | 1,3-(CH₃)₂ | CH₂ | H | CH₂CH₂ | H |
| x-8 | 1-CH₃, 3-Cyclopropyl | CH₂ | H | CH₂CH₂ | H |
| x-8 | 1-CH₃, 3-Cyclopropyl | CH(CH₃) | H | CH₂CH₂ | H |
| x-8 | 1-CH₃, 3-Cyclopropyl | CH₂ | 3-F | CH₂CH₂ | H |
| x-8 | 1,3-(CH₃)₂ | CH₂ | H | CH(CH₃)CH(CH₃) | 4-Cl |
| x-8 | 1,3-(CH₃)₂ | CH₂ | H | CH₂CH(CH₃) | 3,5-(CH₃)₂ |
| x-8 | 1,4-(CH₃)₂ | CH₂ | H | CH₂CH₂ | H |
| x-8 | 1,4-(CH₃)₂ | CH₂CH₂ | H | CH₂CH₂CH₂ | H |
| x-8 | 1-CH₃, 3-Cyclopropyl | CH₂ | H | CH₂CH(CH₃) | 4-Cl |
| x-9 | 1-CH₃ | CH₂ | H | CH₂CH₂ | H |
| x-9 | 1,3-(CH₃)₂ | CH₂ | H | CH₂CH₂ | H |
| x-9 | 1,5-(CH₃)₂ | CH₂ | H | CH₂CH₂ | H |
| x-9 | 1,3-(CH₃)₂ | CH₂ | 3-F | CH₂CH(CH₃) | H |
| x-9 | 1,5-(CH₃)₂ | CH₂ | 3-CH₃ | CH₂CH(CH₃) | H |
| x-9 | 1,3-(CH₃)₂ | CH₂ | H | CH₂CH₂ | 4-Cl |
| x-9 | 1,5-(CH₃)₂ | CH₂ | H | CH₂CH₂ | 3,5-(CH₃)₂ |
| x-9 | 1,3-(CH₃)₂ | CH(CH₃) | H | CH(CH₃)CH₂CH(CH₃) | H |
| x-9 | 1,5-(CH₃)₂ | CH₂CH₂ | H | CH(CH₃)CH₂ | 4-Cl |
| x-10 | 1-CH₃ | CH₂ | H | CH₂CH₂ | H |
| x-10 | 1,5-(CH₃)₂ | CH₂ | H | CH₂CH₂ | H |
| x-10 | 1-CH₃, 5-Cyclopropyl | CH₂ | H | CH₂CH₂ | H |
| x-10 | 1,4-(CH₃)₂ | CH₂ | H | CH₂CH₂ | H |
| x-10 | 1-CH₃, 5-Cyclopropyl | CH₂ | H | CH(CH₃)CH₂ | 4-Cl |
| x-10 | 1-CH₃, 5-Cyclopropyl | CH₂CH₂ | H | CH₂CH₂CH₂ | H |
| x-10 | 1,5-(CH₃)₂ | CH₂ | H | CH₂CH(CH₃) | 3,5-(CH₃)₂ |
| x-10 | 1,5-(CH₃)₂ | CH₂ | H | CH₂CH₂ | 4-Cl |
| x-11 | — | CH₂ | H | CH₂CH₂ | H |
| x-11 | 3-CH₃ | CH₂ | H | CH₂CH₂ | H |
| x-11 | 5-CH₃ | CH₂ | H | CH₂CH₂ | H |
| x-11 | 3-CH₃ | CH₂ | H | CH₂CH₂ | 4-Cl |
| x-11 | 5-CH₃ | CH₂ | H | CH₂CH₂ | 3,5-(CH₃)₂ |
| x-11 | 3-CH₃ | CH₂ | 3-F | CH(CH₃)CH₂ | 4-Cl |
| x-11 | 5-CH₃ | CH₂ | H | CH₂CH(CH₃) | H |
| x-12 | — | CH₂ | H | CH₂CH₂ | H |
| x-12 | 2-CH₃ | CH₂ | H | CH₂CH₂ | H |
| x-12 | 2-Cyclopropyl | CH₂ | H | CH₂CH₂ | H |
| x-12 | 2-OCH₂CH₃ | CH₂ | H | CH₂CH₂ | H |
| x-12 | 2-CH₃ | CH₂ | H | CH₂CH₂ | 4-Cl |
| x-12 | 2-Cyclopropyl | CH₂ | H | CH₂CH₂ | 4-Cl |
| x-12 | 2-CH₃ | CH₂ | H | CH₂CH₂ | 3,5-(CH₃)₂ |
| x-12 | 2-Cyclopropyl | CH₂ | H | CH₂CH₂ | 3,5-(CH₃)₂ |
| x-12 | 2-CH₃ | CH(CH₃) | H | CH(CH₃)CH₂CH₂ | H |
| x-12 | 2-Cyclopropyl | CH₂ | H | CH₂CH(CH₃) | 4-Cl |
| x-13 | 2-Cyclopropyl | CH₂ | H | CH₂CH₂ | H |
| x-13 | 2-CH₃ | CH₂ | H | CH₂CH₂ | H |
| x-13 | 2-Cyclopropyl | CH₂ | H | CH₂CH₂ | 4-Cl |
| x-13 | 2-CH₃ | CH₂ | H | CH₂CH₂ | 4-Cl |
| x-13 | 2-Cyclopropyl | CH₂ | H | CH₂CH₂ | 3,5-(CH₃)₂ |
| x-13 | 2-CH₃ | CH₂ | H | CH₂CH₂ | 3,5-(CH₃)₂ |
| x-13 | 2-OCH₂CH₃ | CH₂ | H | CH₂CH₂ | H |
| x-13 | 2-CH₃ | CH₂ | H | CH(CH₃)CH(CH₃) | H |

TABLE A-continued

X—A$^1$—O—[benzene with R$^1$]—O—A$^2$—O—N=[ring with R'$_n$]    IA positions 2, 3 on benzene

| x | Substituent on x | A$^1$ | R$^1$ | A$^2$ | R'$_n$ |
|---|---|---|---|---|---|
| x-13 | 2-Cyclopropyl | CH$_2$ | H | CH$_2$CH(CH$_3$) | 4-Cl |
| x-14 | — | CH$_2$ | H | CH$_2$CH$_2$ | H |
| x-14 | 5-CH$_3$ | CH$_2$ | H | CH$_2$CH$_2$ | H |
| x-14 | 5-Cyclopropyl | CH$_2$ | H | CH$_2$CH$_2$ | H |
| x-14 | 4-CH$_3$ | CH$_2$ | H | CH$_2$CH$_2$ | 4-Cl |
| x-14 | 4-Cyclopropyl | CH$_2$ | H | CH$_2$CH$_2$ | 4-Cl |
| x-14 | 5-Cl | CH$_2$ | H | CH$_2$CH$_2$CH(CH$_3$) | H |
| x-14 | 4-OCH$_2$CH$_3$ | CH$_2$ | H | CH$_2$CH$_2$ | 3,5-(CH$_3$)$_2$ |
| x-14 | 5-Cyclopropyl | CH$_2$ | H | CH(CH$_3$)CH(CH$_3$) | 4-Cl |
| x-15 | — | CH$_2$ | H | CH$_2$CH$_2$ | H |
| x-15 | 2-CH$_3$ | CH$_2$ | H | CH$_2$CH$_2$ | H |
| x-15 | 2-Cyclopropyl | CH$_2$ | H | CH$_2$CH$_2$ | H |
| x-15 | 2-OCH$_2$CH$_3$ | CH$_2$ | H | CH$_2$CH$_2$ | H |
| x-15 | 2-Cl | CH$_2$ | H | CH$_2$CH$_2$ | H |
| x-15 | 2-CH$_3$ | CH$_2$ | 3-F | CH$_2$CH(CH$_3$) | H |
| x-15 | 2-Cyclopropyl | CH$_2$CH$_2$ | H | CH(CH$_3$)CH(CH$_3$) | H |
| x-15 | 2-CH$_3$ | CH$_2$ | H | CH$_2$CH$_2$ | 4-Cl |
| x-15 | 2-Cyclopropyl | CH$_2$ | H | CH$_2$CH$_2$ | 4-Cl |
| x-15 | 2-CH$_3$ | CH$_2$ | H | CH$_2$CH$_2$CH$_2$ | 3,5-(CH$_3$)$_2$ |
| x-15 | 2-Cyclopropyl | CH(CH$_3$) | H | CH$_2$CH$_2$ | 3,5-(CH$_3$)$_2$ |
| x-16 | — | CH$_2$ | H | CH$_2$CH$_2$ | H |
| x-16 | 2-CH$_3$ | CH$_2$ | H | CH$_2$CH$_2$ | H |
| x-16 | 2-Cyclopropyl | CH$_2$ | H | CH$_2$CH$_2$ | H |
| x-16 | 2-Cl | CH$_2$ | H | CH$_2$CH$_2$ | H |
| x-16 | 2-OCH$_2$CH$_3$ | CH$_2$ | H | CH$_2$CH$_2$ | H |
| x-16 | 2-CH$_3$ | CH$_2$ | H | CH$_2$CH$_2$ | 4-Cl |
| x-16 | 2-Cyclopropyl | CH$_2$ | H | CH$_2$CH$_2$ | 4-Cl |
| x-16 | 2-CH$_3$ | CH$_2$ | H | CH(CH$_3$)CH$_2$ | 3,5-(CH$_3$)$_2$ |
| x-16 | 2-Cyclopropyl | CH$_2$ | H | CH$_2$CH(CH$_3$) | H |
| x-16 | 2-CH$_3$ | CH$_2$CH$_2$ | 3-F | CH$_2$CH$_2$CH$_2$ | H |
| x-16 | 2-Cyclopropyl | CH$_2$ | H | CH(CH$_3$)CH(CH$_3$) | 4-Cl |
| x-17 | — | CH$_2$ | H | CH$_2$CH$_2$ | H |
| x-17 | 5-Cyclopropyl | CH$_2$ | H | CH$_2$CH$_2$ | H |
| x-17 | 5-CH$_3$ | CH$_2$ | H | CH$_2$CH$_2$ | H |
| x-17 | 5-Cl | CH$_2$ | H | CH$_2$CH$_2$ | H |
| x-17 | 5-OCH$_2$CH$_3$ | CH$_2$ | H | CH$_2$CH$_2$ | H |
| x-17 | 4-Cyclopropyl | CH$_2$ | H | CH$_2$CH$_2$ | H |
| x-17 | 4-CH$_3$ | CH$_2$ | H | CH$_2$CH$_2$ | H |
| x-17 | 4-Cl | CH$_2$ | H | CH$_2$CH$_2$ | H |
| x-17 | 4-OCH$_2$CH$_3$ | CH$_2$ | H | CH$_2$CH$_2$ | H |
| x-17 | 5-Cyclopropyl | CH$_2$ | H | CH$_2$CH$_2$ | 4-Cl |
| x-17 | 5-CH$_3$ | CH(CH$_3$) | 3-CH$_3$ | CH(CH$_3$)CH(CH$_3$) | H |
| x-17 | 4-CH$_3$ | CH$_2$ | H | CH$_2$CH$_2$ | 3,5-(CH$_3$)$_2$ |
| x-17 | 4-Cyclopropyl | CH$_2$CH$_2$ | H | CH$_2$CH$_2$CH(CH$_3$) | H |
| x-17 | 5-Cyclopropyl | CH$_2$ | H | CH$_2$CH(CH$_3$) | 4-Cl |
| x-18 | 1-CH$_3$ | CH$_2$ | H | CH$_2$CH$_2$ | H |
| x-18 | 1,2-(CH$_3$)$_2$ | CH$_2$ | H | CH$_2$CH$_2$ | H |
| x-18 | 1,4-(CH$_3$)$_2$ | CH$_2$ | H | CH$_2$CH$_2$ | H |
| x-18 | 1,2,4-(CH$_3$)$_3$ | CH$_2$ | H | CH$_2$CH$_2$ | H |
| x-18 | 1-CH$_3$, 2-Cyclopropyl | CH$_2$ | H | CH$_2$CH$_2$ | H |
| x-18 | 1-CH$_3$, 2-Cyclopropyl | CH$_2$ | H | CH$_2$CH$_2$ | 4-Cl |
| x-18 | 1-CH$_3$, 2-Cyclopropyl | CH$_2$ | H | CH$_2$CH$_2$ | 3,5-(CH$_3$)$_2$ |
| x-18 | 1,2-(CH$_3$)$_2$ | CH$_2$ | H | CH$_2$CH(CH$_3$) | 4-Cl |
| x-18 | 1-CH$_3$ | CH$_2$CH$_2$ | 3-F | CH$_2$CH$_2$CH$_2$ | H |
| x-18 | 1,2,4-(CH$_3$)$_3$ | CH$_2$ | H | CH(CH$_3$)CH(CH$_3$) | H |
| x-18 | 1,4-(CH$_3$)$_2$ | CH$_2$ | H | CH$_2$CH(CH$_3$) | 4-Cl |
| x-18 | 1-CH$_3$, 2-Cyclopropyl | CH(CH$_3$) | H | CH$_2$CH(CH$_3$) | 3,5-(CH$_3$)$_2$ |
| x-18 | 1-CH$_3$, 2-Cyclopropyl | CH$_2$ | H | CH$_2$CH$_2$CH(CH$_3$) | H |
| x-18 | 1-CH$_3$ | CH$_2$ | H | CH$_2$CH$_2$ | 4-Cl |
| x-19 | 1-CH$_3$ | CH$_2$ | H | CH$_2$CH$_2$ | H |
| x-19 | 1,2-(CH$_3$)$_2$ | CH$_2$ | H | CH$_2$CH$_2$ | H |
| x-19 | 1-CH$_3$, 2-Cyclopropyl | CH$_2$ | H | CH$_2$CH$_2$ | H |
| x-19 | 1-CH$_3$ | CH$_2$ | H | CH$_2$CH$_2$ | 4-Cl |
| x-19 | 1,2-(CH$_3$)$_2$ | CH$_2$ | H | CH$_2$CH$_2$ | 4-Cl |
| x-19 | 1-CH$_3$, 2-Cyclopropyl | CH$_2$ | H | CH$_2$CH$_2$ | 4-Cl |
| x-19 | 1-CH$_3$ | CH$_2$ | H | CH$_2$CH$_2$ | 3,5-(CH$_3$)$_2$ |
| x-19 | 1,2-(CH$_3$)$_2$ | CH$_2$ | H | CH$_2$CH$_2$ | 3,5-(CH$_3$)$_2$ |
| x-19 | 1-CH$_3$, 2-Cyclopropyl | CH$_2$ | H | CH$_2$CH$_2$ | 3,5-(CH$_3$)$_2$ |
| x-19 | 1-CH$_3$ | CH$_2$CH$_2$ | H | CH(CH$_3$)CH$_2$CH$_2$ | H |
| x-19 | 1,2-(CH$_3$)$_2$ | CH(CH$_3$) | H | CH$_2$CH(CH$_3$) | 4-Cl |
| x-19 | 1-CH$_3$, 2-Cyclopropyl | CH$_2$ | H | CH(CH$_3$)CH(CH$_3$) | H |
| x-20 | 1-CH$_3$ | CH$_2$ | H | CH$_2$CH$_2$ | H |
| x-20 | 1,5-(CH$_3$)$_2$ | CH$_2$ | H | CH$_2$CH$_2$ | H |

TABLE A-continued

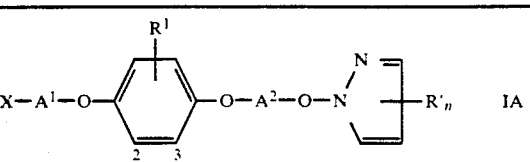

| x | Substituent on x | A¹ | R¹ | A² | R'ₙ |
|---|---|---|---|---|---|
| x-20 | 1-CH₃ | CH₂ | H | CH₂CH₂ | 4-Cl |
| x-20 | 1,5-(CH₃)₂ | CH₂ | H | CH₂CH₂ | 4-Cl |
| x-20 | 1-CH₃ | CH₂ | H | CH₂CH₂CH₂ | 3,5-(CH₃)₂ |
| x-20 | 1,5-(CH₃)₂ | CH₂ | H | CH₂CH(CH₃) | 4-Cl |
| x-20 | 1-CH₃ | CH(CH₃) | H | CH(CH₃)CH(CH₃) | H |
| x-20 | 1,5-(CH₃)₂ | CH₂CH₂ | H | CH(CH₃)CH₂ | H |
| x-21 | — | CH₂ | H | CH₂CH₂ | H |
| x-21 | 4,5-Cl₂ | CH₂ | H | CH₂CH₂ | H |
| x-21 | 4,5-Br₂ | CH₂ | H | CH₂CH₂ | H |
| x-21 | 4,5-(CH₃)₂ | CH₂ | H | CH₂CH₂ | H |
| x-21 | — | CH₂ | H | CH₂CH₂CH(CH₃) | 4-Cl |
| x-21 | 4,5-Cl₂ | CH₂ | H | CH₂CH₂ | 4-Cl |
| x-21 | 4,5-Br₂ | CH(CH₃) | H | CH(CH₃)CH(CH₃) | 3,5-(CH₃)₂ |
| x-21 | 4,5-Cl₂ | CH₂ | 3-F | CH₂CH₂CH(CH₃) | H |
| x-22 | — | CH₂ | H | CH₂CH₂ | H |
| x-22 | 3-CH₃ | CH₂ | H | CH₂CH₂ | H |
| x-22 | 3-Cyclopropyl | CH₂ | H | CH₂CH₂ | H |
| x-22 | 3-OCH₃ | CH₂ | H | CH₂CH₂ | H |
| x-22 | 3-CH₃ | CH₂ | H | CH₂CH₂ | 4-Cl |
| x-22 | 3-Cyclopropyl | CH₂ | H | CH₂CH₂ | 4-Cl |
| x-22 | 3-CH₃ | CH₂ | H | CH₂CH₂ | 3,5-(CH₃)₂ |
| x-22 | 3-Cyclopropyl | CH₂ | H | CH₂CH₂ | 3,5-(CH₃)₂ |
| x-22 | 3-CH₃ | CH₂CH₂ | H | CH(CH₃)CH₂CH₂ | H |
| x-22 | 3-OCH₃ | CH₂ | 3-CH₃ | CH₂CH(CH₃) | H |
| x-22 | 3-Cyclopropyl | CH₂ | H | CH(CH₃)CH(CH₃) | H |
| x-23 | — | CH₂ | H | CH₂CH₂ | H |
| x-23 | 5-CH₃ | CH₂ | H | CH₂CH₂ | H |
| x-23 | 5-CH₂CH₃ | CH₂ | H | CH₂CH₂ | H |
| x-23 | 5-CH(CH₃)₂ | CH₂ | H | CH₂CH₂ | H |
| x-23 | 5-Cyclopropyl | CH₂ | H | CH₂CH₂ | H |
| x-23 | 5-Cl | CH₂ | H | CH₂CH₂ | H |
| x-23 | 5-OCH₂CH₃ | CH₂ | H | CH₂CH₂ | H |
| x-23 | 5-CH₃ | CH₂ | H | CH₂CH₂ | 4-Cl |
| x-23 | 5-CH₃ | CH₂ | H | CH(CH₃)CH(CH₃) | 4-Cl |
| x-23 | 5-Cyclopropyl | CH₂ | H | CH₂CH(CH₃) | 3,5-(CH₃)₂ |
| x-23 | 5-CH(CH₃)₂ | CH₂ | H | CH₂CH₂CH₂ | 4-Cl |
| x-23 | 5-CH₃ | CH(CH₃) | 3-CH₃ | CH(CH₃)CH₂CH₂ | H |
| x-23 | 5-Cyclopropyl | CH₂ | H | CH₂CH₂ | 3,5-(CH₃)₂ |
| x-23 | 5-CH(CH₃)₂ | CH₂ | 3-F | CH₂CH₂ | H |
| x-24 | — | CH₂ | H | CH₂CH₂ | H |
| x-24 | 3-CH₃ | CH₂ | H | CH₂CH₂ | H |
| x-24 | 3-Cyclopropyl | CH₂ | H | CH₂CH₂ | H |
| x-24 | 3-OCH₃ | CH₂ | H | CH₂CH₂ | H |
| x-24 | 3-CH₃ | CH₂ | H | CH₂CH₂ | 4-Cl |
| x-24 | 3-Cyclopropyl | CH₂ | H | CH₂CH₂ | 4-Cl |
| x-24 | 3-CH₃ | CH₂ | H | CH₂CH₂ | 3,5-(CH₃)₂ |
| x-24 | 3-Cyclopropyl | CH₂ | H | CH₂CH₂ | 3,5-(CH₃)₂ |
| x-24 | 3-CH₃ | CH₂CH₂ | H | CH(CH₃)CH₂CH₂ | H |
| x-24 | 3-OCH₃ | CH₂ | 3-F | CH₂CH(CH₃) | H |
| x-24 | 3-Cyclopropyl | CH₂ | H | CH(CH₃)CH(CH₃) | H |
| x-25 | 5-CH₃ | CH₂ | H | CH₂CH₂ | H |
| x-25 | 5-CH₂CH₃ | CH₂ | H | CH₂CH₂ | H |
| x-25 | 5-CH(CH₃)₂ | CH₂ | H | CH₂CH₂ | H |
| x-25 | 5-Cyclopropyl | CH₂ | H | CH₂CH₂ | H |
| x-25 | 5-OCH₃ | CH₂ | H | CH₂CH₂ | H |
| x-25 | 5-OCH₂CH₃ | CH₂ | H | CH₂CH₂ | H |
| x-25 | 5-Cyclopropyl | CH₂ | H | CH₂CH₂ | 3,5-(CH₃)₂ |
| x-25 | 5-CH₃ | CH₂ | H | CH₂CH₂ | 4-Cl |
| x-25 | 5-CH(CH₃)₂ | CH₂ | H | CH₂CH₂ | 4-Cl |
| x-25 | 5-Cyclopropyl | CH₂ | H | CH₂CH₂ | 4-Cl |
| x-25 | 5-CH₃ | CH₂ | H | CH(CH₃)CH₂ | H |
| x-25 | 5-Cyclopropyl | CH₂ | 3-F | CH(CH₃)CH₂ | H |
| x-25 | 5-OCH₂CH₃ | CH₂ | H | CH₂CH(CH₃) | H |
| x-25 | 5-Cyclopropyl | CH(CH₃) | 3-CH₃ | CH₂CH(CH₃) | H |
| x-25 | 5-CH(CH₃)₂ | CH₂ | H | CH₂CH(CH₃) | 4-Cl |
| x-25 | 5-CH₃ | CH₂ | H | CH₂CH(CH₃) | 4-Cl |
| x-25 | 5-Cyclopropyl | CH₂CH₂ | H | CH(CH₃)CH(CH₃) | 3,5-(CH₃)₂ |
| x-25 | 5-Cyclopropyl | CH₂ | H | CH₂CH₂CH₂ | H |
| x-26 | 1-CH₃ | CH₂ | H | CH₂CH₂ | H |
| x-26 | 1,5-(CH₃)₂ | CH₂ | H | CH₂CH₂ | H |
| x-26 | 1-CH₃, 5-Cyclopropyl | CH₂ | H | CH₂CH₂ | H |
| x-26 | 1-CH₃ | CH₂ | H | CH(CH₃)CH(CH₃) | 4-Cl |
| x-26 | 1,5-(CH₃)₂ | CH₂ | H | CH₂CH₂CH(CH₃) | 4-Cl |

TABLE A-continued $$\text{X—A}^1\text{—O—}\underset{2\quad 3}{\text{C}_6\text{H}_3(\text{R}^1)}\text{—O—A}^2\text{—O—N(N=)(pyrazole)—R'}_n \quad \text{IA}$$

| x | Substituent on x | A¹ | R¹ | A² | R'ₙ |
|---|---|---|---|---|---|
| x-26 | 1-CH₃, 5-Cyclopropyl | CH₂ | H | CH₂CH₂ | 3,5-(CH₃)₂ |
| x-26 | 1-CH₃ | CH(CH₃) | H | CH₂CH₂CH₂ | H |
| x-26 | 1-CH₃, 5-Cyclopropyl | CH₂CH₂ | 3-F | CH₂CH₂ | 4-Cl |
| x-27 | — | CH₂ | H | CH₂CH₂ | H |
| x-27 | 2-Cl | CH₂ | H | CH₂CH₂ | H |
| x-27 | 2,5-(CH₃)₂ | CH₂ | H | CH₂CH₂ | H |
| x-27 | — | CH₂ | H | CH₂CH₂ | 4-Cl |
| x-27 | 2-Cl | CH₂ | H | CH₂CH₂ | 4-Cl |
| x-27 | 2,5-(CH₃)₂ | CH₂ | H | CH₂CH₂ | 4-Cl |
| x-27 | — | CH(CH₃) | 3-F | CH(CH₃)CH₂CH₂ | H |
| x-27 | — | CH₂ | H | CH₂CH(CH₃) | 3,5-(CH₃)₂ |
| x-28 | 1-CH₃ | CH₂ | H | CH₂CH₂ | H |
| x-28 | 1,5-(CH₃)₂ | CH₂ | H | CH₂CH₂ | H |
| x-28 | 1-CH₃, 5-Cyclopropyl | CH₂ | H | CH₂CH₂ | H |
| x-28 | 1-CH₃ | CH₂ | H | CH₂CH₂ | 4-Cl |
| x-28 | 1,5-(CH₃)₂ | CH₂ | H | CH₂CH₂ | 4-Cl |
| x-28 | 1-CH₃, 5-Cyclopropyl | CH₂ | H | CH₂CH₂ | 4-Cl |
| x-28 | 1-CH₃ | CH₂ | H | CH₂CH(CH₃) | 3,5-(CH₃)₂ |
| x-28 | 1,5-(CH₃)₂ | CH₂ | H | CH₂CH(CH₃) | 3,5-(CH₃)₂ |
| x-28 | 1-CH₃, 5-Cyclopropyl | CH₂ | H | CH₂CH(CH₃) | 3,5-(CH₃)₂ |
| x-28 | 1-CH₃ | CH₂CH₂ | H | CH₂CH₂CH₂ | H |
| x-29 | 1-CH₃ | CH₂ | H | CH₂CH₂ | H |
| x-29 | 1,3-(CH₃)₂ | CH₂ | H | CH₂CH₂ | H |
| x-29 | 1-CH₃, 3-Cyclopropyl | CH₂ | H | CH₂CH₂ | H |
| x-29 | 1-CH₃ | CH₂ | H | CH₂CH₂ | 4-Cl |
| x-29 | 1,3-(CH₃)₂ | CH₂ | H | CH₂CH₂ | 4-Cl |
| x-29 | 1-CH₃, 3-Cyclopropyl | CH₂ | H | CH₂CH₂ | 4-Cl |
| x-29 | 1-CH₃ | CH₂ | H | CH₂CH₂CH₂ | 3,5-(CH₃)₂ |
| x-30 | — | CH₂ | H | CH₂CH₂ | H |
| x-30 | 3,5-(CH₃)₂ | CH₂ | H | CH₂CH₂ | H |
| x-30 | — | CH₂ | H | CH₂CH₂ | 4-Cl |
| x-30 | 3,5-(CH₃)₂ | CH₂ | H | CH₂CH₂ | 4-Cl |
| x-30 | — | CH₂ | 3-F | CH(CH₃)CH₂ | H |
| x-30 | 3,5-(CH₃)₂ | CH(CH₃) | H | CH₂CH(CH₃) | H |
| x-30 | — | CH₂ | H | CH₂CH(CH₃) | 3,5-(CH₃)₂ |
| x-30 | 3,5-(CH₃)₂ | CH₂CH₂ | H | CH₂CH₂CH₂ | H |

TABLE B $$\text{X—A}^1\text{—O—}\underset{2\quad 3}{\text{C}_6\text{H}_3(\text{R}^1)}\text{—O—A}^2\text{—O—(2-pyridyl)—R'}_n \quad \text{IA}$$

| x | Substituent on x | A¹ | R¹ | A² | R'ₙ |
|---|---|---|---|---|---|
| x-1 | — | CH₂ | H | CH₂CH₂ | H |
| x-1 | — | CH(CH₃) | H | CH₂CH₂ | H |
| x-1 | — | CH(CH₂CH₃) | H | CH₂CH₂ | H |
| x-1 | — | CH₂ | 3-F | CH₂CH₂ | H |
| x-1 | — | CH₂CH₂ | H | CH₂CH₂ | H |
| x-1 | — | CH₂ | H | CH(CH₃)CH₂ | H |
| x-1 | — | CH₂ | H | CH₂CH(CH₃) | H |
| x-1 | — | CH₂ | H | CH₂CH₂CH(CH₃) | H |
| x-1 | 5-CH₃ | CH₂ | H | CH₂CH₂ | H |
| x-1 | 4-CH₃ | CH₂ | H | CH₂CH₂ | H |
| x-1 | 3-CH₃ | CH₂ | H | CH₂CH₂ | H |
| x-1 | 5-Cl | CH₂ | H | CH₂CH(CH₃) | H |
| x-1 | 5-Br | CH₂ | H | CH₂CH(CH₃) | H |
| x-1 | 4-Cl | CH₂ | H | CH₂CH(CH₃) | H |
| x-1 | 4-Br | CH₂ | H | CH₂CH(CH₃) | H |
| x-1 | 5-Cyclopropyl | CH₂ | H | CH₂CH₂ | H |
| x-1 | 4-Cyclopropyl | CH₂ | H | CH₂CH₂ | H |
| x-1 | 4,5-Dichloro | CH₂ | H | CH₂CH(CH₃) | H |
| x-1 | 5-Br | CH₂ | H | CH₂CH(CH₃) | 6-CH₃ |
| x-1 | 5-Br | CH₂ | H | CH₂CH(CH₃) | 5-NO₂ |
| x-1 | 4,5-Dichloro | CH₂ | 3-F | CH(CH₃)CH₂ | H |
| x-1 | 5-CH₃ | CH₂ | H | CH₂CH(CH₃) | 6-CH₃ |

TABLE B-continued $$X-A^1-O-\underset{2\;\;3}{\bigcirc}^{R^1}-O-A^2-O-\underset{N}{\bigcirc}-R'_n \qquad IA$$

| x | Substituent on x | A¹ | R¹ | A² | R'ₙ |
|---|---|---|---|---|---|
| x-1 | 5-Br | CH₂ | H | CH₂CH(CH₃) | 5-NO₂ |
| x-2 | — | CH₂ | H | CH₂CH₂ | H |
| x-2 | 4-Cyclopropyl | CH₂ | H | CH₂CH(CH₃) | H |
| x-2 | 5-Cyclopropyl | CH(CH₃) | H | CH(CH₃)CH₂ | H |
| x-2 | 4-Cl | CH₂ | H | CH₂CH(CH₃) | H |
| x-2 | 5-Br | CH₂ | H | CH₂CH(CH₃) | H |
| x-2 | 4,5-Dichloro | CH₂CH₂ | H | CH₂CH₂ | H |
| x-2 | 4,5-Dibromo | CH₂ | 3-F | CH₂CH(CH₃) | H |
| x-2 | 5-Br | CH(CH₂CH₃) | H | CH₂CH(CH₃) | H |
| x-2 | 5-Br | CH₂ | H | CH₂CH₂ | 6-CH₃ |
| x-2 | 4-Cl | CH₂ | 3-F | CH(CH₃)CH(CH₃) | 5-NO₂ |
| x-2 | 5-Cyclopropyl | CH₂ | H | CH₂CH(CH₃) | 6-CH₃ |
| x-2 | 4-Cyclopropyl | CH₂CH₂ | H | CH₂CH₂CH₂ | H |
| x-3 | 3-CH₃ | CH₂ | H | CH₂CH(CH₃) | H |
| x-3 | 3-CH₂CH₃ | CH₂ | H | CH₂CH(CH₃) | H |
| x-3 | 3-CH(CH₃)₂ | CH₂ | H | CH₂CH(CH₃) | H |
| x-3 | 3-Cyclopropyl | CH₂ | H | CH₂CH(CH₃) | H |
| x-3 | 3-OCH₂CH₃ | CH₂ | H | CH₂CH(CH₃) | H |
| x-3 | 3-CH₂OCH₃ | CH₂ | H | CH₂CH(CH₃) | H |
| x-3 | 3-CF₃ | CH₂ | H | CH₂CH(CH₃) | H |
| x-3 | 3-CH₃ | CH₂ | H | CH₂CH₂ | 6-CH₃ |
| x-3 | 3-Cyclopropyl | CH₂ | H | CH₂CH₂ | 5-NO₂ |
| x-3 | 3-CH(CH₃)₂ | CH₂ | H | CH₂CH(CH₃) | 6-CH₃ |
| x-3 | 3-CH₃ | CH₂ | H | CH(CH₃)CH₂CH₂ | H |
| x-3 | 3-Cyclopropyl | CH₂CH₂CH₂ | H | CH₂CH(CH₃) | H |
| x-3 | 3-CF₃ | CH₂CH₂ | 3-F | CH₂CH(CH₃) | 6-CH₃ |
| x-3 | 3-OCH₂CH₃ | CH(CH₃) | H | CH(CH₃)CH(CH₃) | H |
| x-3 | 3-CH₂CH₃ | CH₂ | 3-CH₃ | CH₂CH₂ | 5-NO₂ |
| x-4 | — | CH₂ | H | CH₂CH₂ | H |
| x-4 | 5-CH₃ | CH₂ | H | CH₂CH(CH₃) | H |
| x-4 | 3-CH₃ | CH₂ | H | CH₂CH(CH₃) | H |
| x-4 | 3-CH(CH₃)₂ | CH₂ | H | CH₂CH(CH₃) | H |
| x-4 | 3-OCH₂CH₃ | CH(CH₃) | H | CH(CH₃)CH₂ | 6-CH₃ |
| x-4 | 5-OCH₂CH₃ | CH₂ | 3-F | CH(CH₃)CH₂ | 5-NO₂ |
| x-4 | 5-CH(CH₃)₂ | CH₂CH₂ | H | CH₂CH₂CH₂ | H |
| x-5 | — | CH₂ | H | CH₂CH(CH₃) | H |
| x-5 | 5-CH₃ | CH₂ | H | CH₂CH(CH₃) | H |
| x-5 | 5-Cyclopropyl | CH₂ | H | CH₂CH(CH₃) | H |
| x-5 | 5-OCH₂CH₃ | CH₂CH₂ | H | CH₂CH(CH₃) | H |
| x-5 | 5-Cyclopropyl | CH(CH₃) | H | CH₂CH₂ | 6-CH₃ |
| x-5 | 5-Cyclopropyl | CH₂ | H | CH(CH₃)CH₂ | 5-NO₂ |
| x-5 | 5-CH₃ | CH(CH₃) | 3-F | CH₂CH(CH₃) | H |
| x-5 | 5-CH₃ | CH₂CH₂CH₂ | H | CH₂CH₂CH₂ | H |
| x-5 | 5-OCH₂CH₃ | CH₂ | H | CH₂CH(CH₃) | 6-CH₃ |
| x-6 | — | CH₂ | 3-F | CH₂CH(CH₃) | H |
| x-6 | 3-CH₃ | CH₂ | H | CH₂CH(CH₃) | H |
| x-6 | 3-Cyclopropyl | CH₂ | H | CH₂CH(CH₃) | H |
| x-6 | 3-OCH₂CH₃ | CH₂ | H | CH₂CH₂ | H |
| x-6 | 3-Cyclopropyl | CH(CH₃) | H | CH(CH₃)CH₂ | H |
| x-6 | 3-Cyclopropyl | CH₂CH₂ | H | CH₂CH(CH₃) | 6-CH₃ |
| x-6 | 3-CH₃ | CH₂ | H | CH₂CH₂CH₂ | 5-NO₂ |
| x-6 | 3-CH₃ | CH₂ | 3-CH₃ | CH₂CH₂ | H |
| x-6 | 3-Cyclopropyl | CH₂ | H | CH(CH₃)CH(CH₃) | H |
| x-7 | — | CH₂ | H | CH₂CH(CH₃) | H |
| x-7 | 3-CH₃ | CH₂ | H | CH₂CH(CH₃) | H |
| x-7 | 3-CH₃ | CH₂ | 3-CH₃ | CH(CH₃)CH₂ | H |
| x-7 | 3-CH₃ | CH₂ | H | CH(CH₃)CH₂CH(CH₃) | H |
| x-7 | 3-CH₃ | CH(CH₃) | H | CH₂CH₂ | 6-CH₃ |
| x-7 | 3-CH₃ | CH₂ | H | CH₂CH(CH₃) | 6-CH₃ |
| x-8 | 1-CH₃ | CH₂ | H | CH₂CH(CH₃) | H |
| x-8 | 1,3-(CH₃)₂ | CH₂ | H | CH₂CH(CH₃) | H |
| x-8 | 1-CH₃, 3-Cyclopropyl | CH₂ | H | CH₂CH(CH₃) | H |
| x-8 | 1-CH₃, 3-Cyclopropyl | CH(CH₃) | H | CH₂CH₂ | H |
| x-8 | 1-CH₃, 3-Cyclopropyl | CH₂ | 3-F | CH₂CH(CH₃) | H |
| x-8 | 1,3-(CH₃)₂ | CH₂ | H | CH(CH₃)CH(CH₃) | 6-CH₃ |
| x-8 | 1,3-(CH₃)₂ | CH₂ | H | CH₂CH₂CH₂ | 5-NO₂ |
| x-8 | 1,4-(CH₃)₂ | CH₂ | H | CH₂CH(CH₃) | H |
| x-8 | 1,4-(CH₃)₂ | CH₂CH₂ | H | CH₂CH(CH₃) | H |
| x-8 | 1-CH₃, 3-Cyclopropyl | CH₂ | H | CH₂CH(CH₃) | 6-CH₃ |
| x-9 | 1-CH₃ | CH₂ | H | CH₂CH(CH₃) | H |
| x-9 | 1,3-(CH₃)₂ | CH₂ | H | CH₂CH(CH₃) | H |
| x-9 | 1,5-(CH₃)₂ | CH₂ | H | CH₂CH(CH₃) | H |

TABLE B-continued

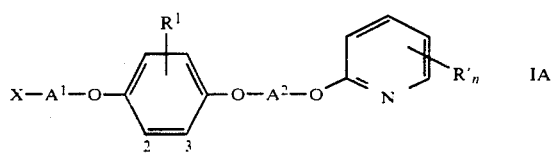

| x | Substituent on x | A¹ | R¹ | A² | R'ₙ |
|---|---|---|---|---|---|
| x-9 | 1,3-(CH₃)₂ | CH₂ | 3-F | CH₂CH(CH₃) | 6-CH₃ |
| x-9 | 1,5-(CH₃)₂ | CH₂ | 3-CH₃ | CH₂CH(CH₃) | 5-NO₂ |
| x-9 | 1,3-(CH₃)₂ | CH₂ | H | CH₂CH₂ | H |
| x-9 | 1,5-(CH₃)₂ | CH₂ | H | CH₂CH₂ | H |
| x-9 | 1,3-(CH₃)₂ | CH(CH₃) | H | CH(CH₃)CH(CH₃) | H |
| x-9 | 1,5-(CH₃)₂ | CH₂CH₂ | H | CH(CH₃)CH(CH₃) | H |
| x-10 | 1-CH₃ | CH₂ | H | CH₂CH(CH₃) | H |
| x-10 | 1,5-(CH₃)₂ | CH₂ | H | CH₂CH(CH₃) | H |
| x-10 | 1-CH₃, 5-Cyclopropyl | CH₂ | H | CH₂CH(CH₃) | H |
| x-10 | 1,4-(CH₃)₂ | CH₂ | H | CH₂CH(CH₃) | H |
| x-10 | 1-CH₃, 5-Cyclopropyl | CH₂ | H | CH(CH₃)CH₂ | 6-CH₃ |
| x-10 | 1-CH₃, 5-Cyclopropyl | CH₂CH₂ | H | CH₂CH₂ | 5-NO₂ |
| x-10 | 1,5-(CH₃)₂ | CH₂ | H | CH₂CH(CH₃) | 6-CH₃ |
| x-10 | 1,5-(CH₃)₂ | CH₂ | H | CH₂CH₂CH₂ | 6-CH₃ |
| x-11 | — | CH₂ | H | CH₂CH(CH₃) | H |
| x-11 | 3-CH₃ | CH₂ | H | CH₂CH(CH₃) | H |
| x-11 | 5-CH₃ | CH₂ | H | CH₂CH(CH₃) | H |
| x-11 | 3-CH₃ | CH₂ | H | CH₂CH₂ | H |
| x-11 | 5-CH₃ | CH₂ | H | CH₂CH₂ | H |
| x-11 | 3-CH₃ | CH₂ | 3-F | CH(CH₃)CH₂ | 6-CH₃ |
| x-11 | 5-CH₃ | CH₂ | H | CH₂CH(CH₃) | 5-NO₂ |
| x-12 | — | CH₂ | H | CH₂CH(CH₃) | H |
| x-12 | 2-CH₃ | CH₂ | H | CH₂CH(CH₃) | H |
| x-12 | 2-Cyclopropyl | CH₂ | H | CH₂CH(CH₃) | H |
| x-12 | 2-OCH₂CH₃ | CH₂ | H | CH₂CH(CH₃) | H |
| x-12 | 2-CH₃ | CH₂ | H | CH₂CH₂ | H |
| x-12 | 2-Cyclopropyl | CH₂ | H | CH₂CH₂ | H |
| x-12 | 2-CH₃ | CH₂ | H | CH₂CH(CH₃) | 6-CH₃ |
| x-12 | 2-Cyclopropyl | CH₂ | H | CH₂CH(CH₃) | 6-CH₃ |
| x-12 | 2-CH₃ | CH(CH₃) | H | CH(CH₃)CH₂ | 5-NO₂ |
| x-12 | 2-Cyclopropyl | CH₂ | H | CH₂CH(CH₃) | 5-NO₂ |
| x-13 | 2-Cyclopropyl | CH₂ | H | CH₂CH(CH₃) | H |
| x-13 | 2-CH₃ | CH₂ | H | CH₂CH(CH₃) | H |
| x-13 | 2-Cyclopropyl | CH₂ | H | CH₂CH₂ | H |
| x-13 | 2-CH₃ | CH₂ | H | CH₂CH₂ | H |
| x-13 | 2-Cyclopropyl | CH₂ | H | CH₂CH(CH₃) | 6-CH₃ |
| x-13 | 2-CH₃ | CH₂ | H | CH₂CH(CH₃) | 5-NO₂ |
| x-13 | 2-OCH₂CH₃ | CH₂ | H | CH₂CH(CH₃) | H |
| x-13 | 2-CH₃ | CH₂ | H | CH(CH₃)CH₂ | H |
| x-13 | 2-Cyclopropyl | CH₂ | H | CH₂CH₂CH₂ | 6-CH₃ |
| x-14 | — | CH₂ | H | CH₂CH(CH₃) | H |
| x-14 | 5-CH₃ | CH₂ | H | CH₂CH(CH₃) | H |
| x-14 | 5-Cyclopropyl | CH₂ | H | CH₂CH(CH₃) | H |
| x-14 | 4-CH₃ | CH₂ | H | CH₂CH(CH₃) | H |
| x-14 | 4-Cyclopropyl | CH₂ | H | CH₂CH(CH₃) | H |
| x-14 | 5-Cl | CH₂ | H | CH₂CH(CH₃) | H |
| x-14 | 4-OCH₂CH₃ | CH₂ | H | CH₂CH(CH₃) | H |
| x-14 | 5-Cyclopropyl | CH₂ | H | CH(CH₃)CH₂ | 6-CH₃ |
| x-15 | — | CH₂ | H | CH₂CH(CH₃) | H |
| x-15 | 2-CH₃ | CH₂ | H | CH₂CH(CH₃) | H |
| x-15 | 2-Cyclopropyl | CH₂ | H | CH₂CH(CH₃) | H |
| x-15 | 2-OCH₂CH₃ | CH₂ | H | CH₂CH(CH₃) | H |
| x-15 | 2-Cl | CH₂ | H | CH₂CH(CH₃) | H |
| x-15 | 2-CH₃ | CH₂ | 3-F | CH₂CH₂ | 5-NO₂ |
| x-15 | 2-Cyclopropyl | CH₂CH₂ | H | CH(CH₃)CH₂CH₂ | H |
| x-15 | 2-CH₃ | CH₂ | H | CH₂CH₂ | 6-CH₃ |
| x-15 | 2-Cyclopropyl | CH₂ | H | CH₂CH₂ | 6-CH₃ |
| x-15 | 2-CH₃ | CH₂ | H | CH₂CH(CH₃) | 5-NO₂ |
| x-15 | 2-Cyclopropyl | CH(CH₃) | H | CH₂CH(CH₃) | H |
| x-16 | — | CH₂ | H | CH₂CH(CH₃) | H |
| x-16 | 2-CH₃ | CH₂ | H | CH₂CH(CH₃) | H |
| x-16 | 2-Cyclopropyl | CH₂ | H | CH₂CH(CH₃) | H |
| x-16 | 2-Cl | CH₂ | H | CH₂CH(CH₃) | H |
| x-16 | 2-OCH₂CH₃ | CH₂ | H | CH₂CH(CH₃) | H |
| x-16 | 2-CH₃ | CH₂ | H | CH₂CH₂ | 6-CH₃ |
| x-16 | 2-Cyclopropyl | CH₂ | H | CH₂CH₂ | 6-CH₃ |
| x-16 | 2-CH₃ | CH₂ | H | CH(CH₃)CH₂CH₂ | H |
| x-16 | 2-Cyclopropyl | CH₂ | H | CH₂CH(CH₃) | 5-NO₂ |
| x-16 | 2-CH₃ | CH₂CH₂ | 3-F | CH₂CH₂ | H |
| x-16 | 2-Cyclopropyl | CH₂ | H | CH(CH₃)CH(CH₃) | H |
| x-17 | — | CH₂ | H | CH₂CH(CH₃) | H |
| x-17 | 5-Cyclopropyl | CH₂ | H | CH₂CH(CH₃) | H |

TABLE B-continued

| x | Substituent on x | A¹ | R¹ | A² | R'ₙ |
|---|---|---|---|---|---|
| x-17 | 5-CH₃ | CH₂ | H | CH₂CH(CH₃) | H |
| x-17 | 5-Cl | CH₂ | H | CH₂CH(CH₃) | H |
| x-17 | 5-OCH₂CH₃ | CH₂ | H | CH₂CH(CH₃) | H |
| x-17 | 4-Cyclopropyl | CH₂ | H | CH₂CH(CH₃) | H |
| x-17 | 4-CH₃ | CH₂ | H | CH₂CH(CH₃) | H |
| x-17 | 4-Cl | CH₂ | H | CH₂CH(CH₃) | H |
| x-17 | 4-OCH₂CH₃ | CH₂ | H | CH₂CH(CH₃) | H |
| x-17 | 5-Cyclopropyl | CH₂ | H | CH₂CH(CH₃) | 6-CH₃ |
| x-17 | 5-CH₃ | CH(CH₃) | 3-CH₃ | CH(CH₃)CH₂ | H |
| x-17 | 4-CH₃ | CH₂ | H | CH₂CH₂ | 5-NO₂ |
| x-17 | 4-Cyclopropyl | CH₂CH₂ | H | CH₂CH₂CH₂ | H |
| x-17 | 5-Cyclopropyl | CH₂ | H | CH₂CH(CH₃) | 5-NO₂ |
| x-18 | 1-CH₃ | CH₂ | H | CH₂CH(CH₃) | H |
| x-18 | 1,2-(CH₃)₂ | CH₂ | H | CH₂CH(CH₃) | H |
| x-18 | 1,4-(CH₃)₂ | CH₂ | H | CH₂CH(CH₃) | H |
| x-18 | 1,2,4-(CH₃)₃ | CH₂ | H | CH₂CH(CH₃) | H |
| x-18 | 1-CH₃, 2-Cyclopropyl | CH₂ | H | CH₂CH(CH₃) | H |
| x-18 | 1-CH₃, 2-Cyclopropyl | CH₂ | H | CH₂CH(CH₃) | 6-CH₃ |
| x-18 | 1-CH₃, 2-Cyclopropyl | CH₂ | H | CH₂CH(CH₃) | 5-NO₂ |
| x-18 | 1,2-(CH₃)₂ | CH₂ | H | CH₂CH₂ | H |
| x-18 | 1-CH₃ | CH₂CH₂ | 3-F | CH₂CH₂CH₂ | H |
| x-18 | 1,2,4-(CH₃)₃ | CH₂ | H | CH(CH₃)CH(CH₃) | H |
| x-18 | 1,4-(CH₃)₂ | CH₂ | H | CH₂CH₂ | 6-CH₃ |
| x-18 | 1-CH₃, 2-Cyclopropyl | CH(CH₃) | H | CH₂CH(CH₃) | H |
| x-18 | 1-CH₃, 2-Cyclopropyl | CH₂ | H | CH₂CH₂ | 5-NO₂ |
| x-18 | 1-CH₃ | CH₂ | H | CH₂CH(CH₃) | 6-CH₃ |
| x-19 | 1-CH₃ | CH₂ | H | CH₂CH(CH₃) | H |
| x-19 | 1,2-(CH₃)₂ | CH₂ | H | CH₂CH(CH₃) | H |
| x-19 | 1-CH₃, 2-Cyclopropyl | CH₂ | H | CH₂CH(CH₃) | H |
| x-19 | 1-CH₃ | CH₂ | H | CH₂CH(CH₃) | 6-CH₃ |
| x-19 | 1,2-(CH₃)₂ | CH₂ | H | CH₂CH(CH₃) | 6-CH₃ |
| x-19 | 1-CH₃, 2-Cyclopropyl | CH₂ | H | CH₂CH(CH₃) | 6-CH₃ |
| x-19 | 1-CH₃ | CH₂ | H | CH₂CH₂ | H |
| x-19 | 1,2-(CH₃)₂ | CH₂ | H | CH₂CH₂ | H |
| x-19 | 1-CH₃, 2-Cyclopropyl | CH₂ | H | CH₂CH₂ | H |
| x-19 | 1-CH₃ | CH₂CH₂ | H | CH(CH₃)CH₂CH₂ | 5-NO₂ |
| x-19 | 1,2-(CH₃)₂ | CH(CH₃) | H | CH₂CH(CH₃) | 5-NO₂ |
| x-19 | 1-CH₃, 2-Cyclopropyl | CH₂ | H | CH(CH₃)CH(CH₃) | H |
| x-20 | 1-CH₃ | CH₂ | H | CH₂CH(CH₃) | H |
| x-20 | 1,5-(CH₃)₂ | CH₂ | H | CH₂CH(CH₃) | H |
| x-20 | 1-CH₃ | CH₂ | H | CH₂CH₂ | H |
| x-20 | 1,5-(CH₃)₂ | CH₂ | H | CH₂CH₂ | H |
| x-20 | 1-CH₃ | CH₂ | H | CH₂CH(CH₃) | 6-CH₃ |
| x-20 | 1,5-(CH₃)₂ | CH₂ | H | CH₂CH(CH₃) | 5-NO₂ |
| x-20 | 1-CH₃ | CH(CH₃) | H | CH(CH₃)CH₂CH(CH₃) | H |
| x-20 | 1,5-(CH₃)₂ | CH₂CH₂ | H | CH(CH₃)CH₂ | H |
| x-21 | — | CH₂ | H | CH₂CH(CH₃) | H |
| x-21 | 4,5-Cl₂ | CH₂ | H | CH₂CH(CH₃) | H |
| x-21 | 4,5-Br₂ | CH₂ | H | CH₂CH(CH₃) | H |
| x-21 | 4,5-(CH₃)₂ | CH₂ | H | CH₂CH(CH₃) | H |
| x-21 | — | CH₂ | H | CH₂CH(CH₃) | 6-CH₃ |
| x-21 | 4,5-Cl₂ | CH₂ | H | CH₂CH(CH₃) | 6-CH₃ |
| x-21 | 4,5-Br₂ | CH(CH₃) | H | CH(CH₃)CH₂CH₂ | H |
| x-21 | 4,5-Cl₂ | CH₂ | 3-F | CH₂CH₂ | 5-NO₂ |
| x-22 | — | CH₂ | H | CH₂CH(CH₃) | H |
| x-22 | 3-CH₃ | CH₂ | H | CH₂CH(CH₃) | H |
| x-22 | 3-Cyclopropyl | CH₂ | H | CH₂CH(CH₃) | H |
| x-22 | 3-OCH₃ | CH₂ | H | CH₂CH(CH₃) | H |
| x-22 | 3-CH₃ | CH₂ | H | CH₂CH₂ | H |
| x-22 | 3-Cyclopropyl | CH₂ | H | CH₂CH₂ | H |
| x-22 | 3-CH₃ | CH₂ | H | CH₂CH(CH₃) | 6-CH₃ |
| x-22 | 3-Cyclopropyl | CH₂ | H | CH₂CH(CH₃) | 5-NO₂ |
| x-22 | 3-CH₃ | CH₂CH₂ | H | CH(CH₃)CH(CH₃) | H |
| x-22 | 3-OCH₃ | CH₂ | 3-CH₃ | CH₂CH₂CH₂ | H |
| x-22 | 3-Cyclopropyl | CH₂ | H | CH(CH₃)CH(CH₃) | 6-CH₃ |
| x-23 | — | CH₂ | H | CH₂CH(CH₃) | H |
| x-23 | 5-CH₃ | CH₂ | H | CH₂CH(CH₃) | H |
| x-23 | 5-CH₂CH₃ | CH₂ | H | CH₂CH(CH₃) | H |
| x-23 | 5-CH(CH₃)₂ | CH₂ | H | CH₂CH(CH₃) | H |
| x-23 | 5-Cyclopropyl | CH₂ | H | CH₂CH(CH₃) | H |
| x-23 | 5-Cl | CH₂ | H | CH₂CH(CH₃) | H |
| x-23 | 5-OCH₂CH₃ | CH₂ | H | CH₂CH(CH₃) | H |

TABLE B-continued

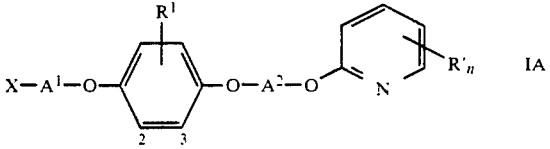

| x | Substituent on x | $A^1$ | $R^1$ | $A^2$ | $R'_n$ |
|---|---|---|---|---|---|
| x-23 | 5-$CH_3$ | $CH_2$ | H | $CH_2CH(CH_3)$ | 6-$CH_3$ |
| x-23 | 5-$CH_3$ | $CH_2$ | H | $CH(CH_3)CH_2$ | H |
| x-23 | 5-Cyclopropyl | $CH_2$ | H | $CH_2CH_2$ | H |
| x-23 | 5-$CH(CH_3)_2$ | $CH_2$ | H | $CH_2CH_2$ | H |
| x-23 | 5-$CH_3$ | $CH(CH_3)$ | 3-$CH_3$ | $CH(CH_3)CH_2$ | H |
| x-23 | 5-Cyclopropyl | $CH_2$ | H | $CH_2CH_2CH(CH_3)$ | H |
| x-23 | 5-$CH(CH_3)_2$ | $CH_2$ | 3-F | $CH_2CH(CH_3)$ | H |
| x-24 | — | $CH_2$ | H | $CH_2CH(CH_3)$ | H |
| x-24 | 3-$CH_3$ | $CH_2$ | H | $CH_2CH(CH_3)$ | H |
| x-24 | 3-Cyclopropyl | $CH_2$ | H | $CH_2CH(CH_3)$ | H |
| x-24 | 3-$OCH_3$ | $CH_2$ | H | $CH_2CH(CH_3)$ | H |
| x-24 | 3-$CH_3$ | $CH_2$ | H | $CH_2CH_2$ | H |
| x-24 | 3-Cyclopropyl | $CH_2$ | H | $CH_2CH_2$ | H |
| x-24 | 3-$CH_3$ | $CH_2$ | H | $CH_2CH(CH_3)$ | 6-$CH_3$ |
| x-24 | 3-Cyclopropyl | $CH_2$ | H | $CH_2CH(CH_3)$ | 6-$CH_3$ |
| x-24 | 3-$CH_3$ | $CH_2CH_2$ | H | $CH(CH_3)CH_2CH_2$ | H |
| x-24 | 3-$OCH_3$ | $CH_2$ | 3-F | $CH_2CH_2$ | 5-$NO_2$ |
| x-24 | 3-Cyclopropyl | $CH_2$ | H | $CH(CH_3)CH_2CH(CH_3)$ | H |
| x-25 | 5-$CH_3$ | $CH_2$ | H | $CH_2CH(CH_3)$ | H |
| x-25 | 5-$CH_2CH_3$ | $CH_2$ | H | $CH_2CH(CH_3)$ | H |
| x-25 | 5-$CH(CH_3)_2$ | $CH_2$ | H | $CH_2CH(CH_3)$ | H |
| x-25 | 5-Cyclopropyl | $CH_2$ | H | $CH_2CH(CH_3)$ | H |
| x-25 | 5-$OCH_3$ | $CH_2$ | H | $CH_2CH(CH_3)$ | H |
| x-25 | 5-$OCH_2CH_3$ | $CH_2$ | H | $CH_2CH(CH_3)$ | H |
| x-25 | 5-Cyclopropyl | $CH_2$ | H | $CH_2CH_2$ | H |
| x-25 | 5-$CH_3$ | $CH_2$ | H | $CH_2CH_2$ | H |
| x-25 | 5-$CH(CH_3)_2$ | $CH_2$ | H | $CH_2CH_2$ | H |
| x-25 | 5-Cyclopropyl | $CH_2$ | H | $CH_2CH(CH_3)$ | 6-$CH_3$ |
| x-25 | 5-$CH_3$ | $CH_2$ | H | $CH(CH_3)CH_2$ | H |
| x-25 | 5-Cyclopropyl | $CH_2$ | 3-F | $CH(CH_3)CH_2$ | H |
| x-25 | 5-$OCH_2CH_3$ | $CH_2$ | H | $CH_2CH(CH_3)$ | 6-$CH_3$ |
| x-25 | 5-Cyclopropyl | $CH(CH_3)$ | 3-$CH_3$ | $CH_2CH_2$ | H |
| x-25 | 5-$CH(CH_3)_2$ | $CH_2$ | H | $CH_2CH_2CH_2$ | H |
| x-25 | 5-$CH_3$ | $CH_2$ | H | $CH_2CH(CH_3)$ | 5-$NO_2$ |
| x-25 | 5-Cyclopropyl | $CH_2CH_2$ | H | $CH(CH_3)CH(CH_3)$ | H |
| x-25 | 5-Cyclopropyl | $CH_2$ | H | $CH_2CH_2CH_2$ | H |
| x-26 | 1-$CH_3$ | $CH_2$ | H | $CH_2CH(CH_3)$ | H |
| x-26 | 1,5-$(CH_3)_2$ | $CH_2$ | H | $CH_2CH(CH_3)$ | H |
| x-26 | 1-$CH_3$, 5-Cyclopropyl | $CH_2$ | H | $CH_2CH(CH_3)$ | H |
| x-26 | 1-$CH_3$ | $CH_2$ | H | $CH(CH_3)CH_2$ | H |
| x-26 | 1,5-$(CH_3)_2$ | $CH_2$ | H | $CH_2CH_2$ | 6-$CH_3$ |
| x-26 | 1-$CH_3$, 5-Cyclopropyl | $CH_2$ | H | $CH_2CH_2CH_2$ | H |
| x-26 | 1-$CH_3$ | $CH(CH_3)$ | H | $CH_2CH(CH_3)$ | H |
| x-26 | 1-$CH_3$, 5-Cyclopropyl | $CH_2CH_2$ | 3-F | $CH_2CH_2$ | 5-$NO_2$ |
| x-27 | — | $CH_2$ | H | $CH_2CH(CH_3)$ | H |
| x-27 | 2-Cl | $CH_2$ | H | $CH_2CH(CH_3)$ | H |
| x-27 | 2,5-$(CH_3)_2$ | $CH_2$ | H | $CH_2CH(CH_3)$ | H |
| x-27 | — | $CH_2$ | H | $CH_2CH_2$ | H |
| x-27 | 2-Cl | $CH_2$ | H | $CH_2CH_2$ | H |
| x-27 | 2,5-$(CH_3)_2$ | $CH_2$ | H | $CH_2CH_2$ | 6-$CH_3$ |
| x-27 | — | $CH(CH_3)$ | 3-F | $CH(CH_3)CH(CH_3)$ | H |
| x-27 | — | $CH_2$ | H | $CH_2CH(CH_3)$ | 5-$NO_2$ |
| x-28 | 1-$CH_3$ | $CH_2$ | H | $CH_2CH(CH_3)$ | H |
| x-28 | 1,5-$(CH_3)_2$ | $CH_2$ | H | $CH_2CH(CH_3)$ | H |
| x-28 | 1-$CH_3$, 5-Cyclopropyl | $CH_2$ | H | $CH_2CH(CH_3)$ | H |
| x-28 | 1-$CH_3$ | $CH_2$ | H | $CH_2CH_2$ | H |
| x-28 | 1,5-$(CH_3)_2$ | $CH_2$ | H | $CH_2CH_2$ | H |
| x-28 | 1-$CH_3$, 5-Cyclopropyl | $CH_2$ | H | $CH_2CH_2$ | H |
| x-28 | 1-$CH_3$ | $CH_2$ | H | $CH_2CH(CH_3)$ | 6-$CH_3$ |
| x-28 | 1,5-$(CH_3)_2$ | $CH_2$ | H | $CH_2CH(CH_3)$ | 5-$NO_2$ |
| x-28 | 1-$CH_3$, 5-Cyclopropyl | $CH_2$ | H | $CH_2CH(CH_3)$ | 6-$CH_3$ |
| x-28 | 1-$CH_3$ | $CH_2CH_2$ | H | $CH_2CH_2CH_2$ | H |
| x-29 | 1-$CH_3$ | $CH_2$ | H | $CH_2CH(CH_3)$ | H |
| x-29 | 1,3-$(CH_3)_2$ | $CH_2$ | H | $CH_2CH(CH_3)$ | H |
| x-29 | 1-$CH_3$, 3-Cyclopropyl | $CH_2$ | H | $CH_2CH(CH_3)$ | H |
| x-29 | 1-$CH_3$ | $CH_2$ | H | $CH_2CH_2$ | H |
| x-29 | 1,3-$(CH_3)_2$ | $CH_2$ | H | $CH_2CH_2$ | 6-$CH_3$ |
| x-29 | 1-$CH_3$, 3-Cyclopropyl | $CH_2$ | H | $CH_2CH(CH_3)$ | 6-$CH_3$ |
| x-29 | 1-$CH_3$ | $CH_2$ | H | $CH_2CH(CH_3)$ | 5-$NO_2$ |
| x-30 | — | $CH_2$ | H | $CH_2CH(CH_3)$ | H |
| x-30 | 3,5-$(CH_3)_2$ | $CH_2$ | H | $CH_2CH(CH_3)$ | H |
| x-30 | — | $CH_2$ | H | $CH_2CH_2$ | H |

TABLE B-continued

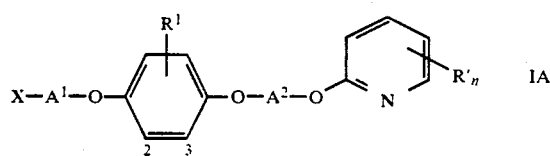

| x | Substituent on x | $A^1$ | $R^1$ | $A^2$ | $R'_n$ |
|---|---|---|---|---|---|
| x-30 | 3,5-$(CH_3)_2$ | $CH_2$ | H | $CH_2CH_2$ | H |
| x-30 | — | $CH_2$ | 3-F | $CH(CH_3)CH_2$ | 6-$CH_3$ |
| x-30 | 3,5-$(CH_3)_2$ | $CH(CH_3)$ | H | $CH_2CH_2CH_2$ | H |
| x-30 | — | $CH_2$ | H | $CH_2CH(CH_3)$ | 6-$CH_3$ |
| x-30 | 3,5-$(CH_3)_2$ | $CH_2CH_2$ | H | $CH_2CH(CH_3)$ | 5-$NO_2$ |

With a view to their use as intermediates for synthesizing the hydroquinone diethers I, the diethers of the formula IV have substituents with the following meanings:

$A^2$ and $R^1$ the radicals mentioned above;

R $C_1$-$C_6$-alkyl as mentioned above, preferably $C_1$-$C_4$-alkyl, especially 1,1-dimethylethyl;

benzyl in which the aromatic radical can carry one to five halogen atoms as mentioned above, preferably fluorine, chlorine and bromine, especially fluorine and chlorine, and/or one to three of the following: cyano, nitro, $C_1$-$C_4$-alkyl as mentioned above, preferably methyl, ethyl and propyl, especially methyl;

$C_1$-$C_4$-alkoxy as mentioned above, preferably $C_1$-$C_2$-alkoxy, especially methoxy;

or $C_1$-$C_4$-alkylthio as mentioned above, preferably $C_1$-$C_2$-alkylthio, especially methylthio, silyl which carries three of the following: $C_1$-$C_6$-alkyl as mentioned above, preferably $C_1$-$C_4$-alkyl, especially methyl, ethyl and 1-methylethyl;

and/or phenyl in which the aromatic radical can carry one to five halogen atoms as mentioned above, preferably fluorine, chlorine and bromine, especially fluorine and chlorine, and/or one to three of the following: cyano, nitro, $C_1$-$C_4$-alkyl as mentioned above, preferably $C_1$-$C_2$-alkyl, especially methyl;

$C_1$-$C_4$-alkoxy as mentioned above, preferably $C_1$-$C_2$-alkoxy, especially methoxy;

or $C_1$-$C_4$-alkylthio as mentioned above, preferably $C_1$-$C_2$-alkylthio, especially methylthio,

Z hydroxyl; halogen as mentioned above, preferably chlorine and bromine, especially bromine; sulfonyl which carries one of the following: $C_1$-$C_{10}$-alkyl, especially $C_1$-$C_6$-alkyl as mentioned above, preferably $C_1$-$C_4$-alkyl, especially methyl, or phenyl in which the aromatic radical can carry one to five halogen atoms as mentioned above, preferably fluorine, chlorine and bromine, especially fluorine and chlorine, and/or one to three of the following: cyano, nitro, $C_1$-$C_4$-alkyl as mentioned above, preferably $C_1$-$C_2$-alkyl, especially methyl;

$C_1$-$C_4$-alkoxy as mentioned above, preferably $C_1$-$C_2$-alkoxy; especially methoxy;

or $C_1$-$C_4$-alkylthio as mentioned above, preferably $C_1$-$C_2$-alkylthio, especially methylthio, or one of the groups mentioned for $R^2$.

With a view to their use as intermediates for synthesizing the hydroquinone diethers I, the monoethers of the formula VI have substituents $R^1$, $R^2$ and $A^2$ with the meanings mentioned above.

The compounds of the formula I are suitable for effectively controlling pests from the classes of insects, arachnids and nematodes. They can be employed as pesticides in crop protection and in the hygiene, store-protection and veterinary sectors.

The insect pests include those from the order of Lepidoptera, for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura, fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hullula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of Coleoptera, for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllo-*

*phaga sp., Phyllopertha horticola, Phyllotreta nemorum, Phyllotreta striolata, Popillia japonica, Sitona lineatus, Sitophilus granaria.*

From the order of Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativaé, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hyoscyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of Thysanoptera, for example *Frankliniella fusca, Frankliniella occidentalis, Frankliniella tritici, Scirtothrips citri, Thrips oryzae, Thrips palmi, Thrips tabaci.*

From the order of Hymenoptera, for example *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of Heteroptera, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis, Thyanta perditor.*

From the order of Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of Isoptera, for example *Calotermes flavicollis, Leucotermes flavipes, Reticulitermes lucifugus, Termes natalensis.*

From the order of Orthoptera, for example *Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of Arachnoidea, for example arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius, Tetranychus urticae.*

From the class of nematodes, for example root knot nematodes, e.g. *Meloidogyne hapla, Meloidogyne incognita, Meloidogyne javanica,* cyst-forming nematodes, e.g. *Globodera rostochiensis, Heterodera avenae, Heterodera glycinae, Heterodera schatii, Heterodera trifolii,* stem and leaf eelworms, e.g. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be applied as such or as formulations thereof or as application forms prepared therefrom, e.g. in the form of directly sprayable solutions, powders, suspensions or dispersions, emulsions, oil dispersions, pastes, dusting or broadcasting agents, or granules by spraying, atomizing, dusting, broadcasting or watering. The application forms depend entirely on the purposes for which they are used; they ought in every case to ensure the finest possible distribution of the novel active ingredients.

Suitable for preparing directly sprayable solutions, emulsions, pastes or oil dispersions are mineral oil fractions of moderate to high boiling points such as kerosene or diesel oil, also coaltar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, tetrachloromethane, cyclohexanol, cyclohexanone, chlorobenzene, isophorone, highly polar solvents, e.g. dimethylformamide, dimethyl sulfoxide, N-methylpyrrolidone and water.

Aqueous application forms can be prepared from emulsion concentrates, pastes or wettable powders (oil dispersions) by adding water. To prepare emulsions, pastes or oil dispersions, the substances can be homogenized, as such or dissolved in an oil or solvent, in water using wetting agents, adhesion promoters, dispersants or emulsifiers. However, it is also possible to prepare concentrates which are composed of active substance, wetting agent, adhesion promoter, dispersant or emulsifier and, where appropriate, solvent or oil and which are suitable for dilution with water.

Examples of surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and the alkali metal and alkaline earth metal salts thereof, salts of sulfated fatty alcohol glycol ethers, products of the condensation of sulfonated naphthalene and naphthalene derivatives with formaldehyde, products of the condensation of naphthalene or naphthalenesulfonic acid with phenol and formaldehyde, polyoxyethylene octylphenol ether, ethoxylated isooctylphenol, octylphenol, nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, broadcasting and dusting agents can be prepared by mixing or grinding the active substances together with a solid carrier.

The formulations generally contain from 0.01 to by weight, preferably from 0.1 to 90% by weight, of the active ingredient. The active ingredients are employed in a purity of from 90 to 100%, preferably from 95 to 100% (according to the NMR spectrum) for this.

Examples of formulations are:

I. 5 parts by weight of compound No. 1.019 are intimately mixed with 95 parts by weight of finely divided kaolin. This results in a dusting agent which contains 5% by weight of active ingredient.

II. 30 parts by weight of compound No. 1.007 are intimately mixed with a mixture of 92 parts by weight of powdered silica gel and 8 parts by weight of liquid paraffin which has been sprayed on the surface of this silica gel. This results in a formulation of the active ingredient with good adhesion (content of active ingredient 23% by weight).

III. 10 parts by weight of compound No. 1.024 are dissolved in a mixture composed of 90 parts by weight of xylene, 6 parts by weight of the adduct of 8 to 10 moles of ethylene oxide and 1 mole of oleic acid N-monoethanolamide, 2 parts by weight of calcium dodecylbenzenesulfonate and 2 parts by weight of the adduct of 40 moles of ethylene oxide and 1 mole of castor oil (content of active ingredient 9% by weight).

IV. 20 parts by weight of compound No. 1.013 are dissolved in a mixture composed of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil (content of active ingredient 16% by weight).

V. 80 parts by weight of compound No. 1.009 are thoroughly mixed with 3 parts by weight of sodium diisobutylnaphthalene-alpha-sulfonate, 10 parts by weight of the sodium salt of a ligninsulfonic acid from a sulfite waste liquor and 7 parts by weight of powdered silica gel and ground in a hammer mill (content of active ingredient 80% by weight).

VI. 90 parts by weight of compound No 1.021 are mixed with 10 parts by weight of N-methyl-α-pyrrolidone to give a solution which is suitable for application in the form of very small drops (content of active ingredient 90% by weight).

VII. 20 parts by weight of compound No. 1.003 are dissolved in a mixture composed of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. A fine dispersion of the solution in 100,000 parts by weight of water contains 0.02% by weight of the active ingredient.

VIII. 20 parts by weight of active ingredient No. 1.001 are thoroughly mixed with 3 parts by weight of sodium diisobutylnaphthalene-α-sulfonate, 17 parts by weight of the sodium salt of a ligninsulfonic acid from a sulfite waste liquor and 60 parts by weight of powdered silica gel and ground in a hammer mill. A fine dispersion of the mixture in 20,000 parts by weight of water contains 0.1% by weight of the active ingredient and can be used for spraying.

Granules, e.g. coated, impregnated and homogeneous granules, can be prepared by binding the active ingredients to solid carriers. Examples of solid carriers are mineral earths such as silica gel, silicic acids, silicates, talc, kaolin, attapulgite, limestone, lime, chalk, bole, loess, clay, dolomite, diatomaceous earth, calcium and magnesium sulfate, magnesium oxide, ground plastics, fertilizers such as, for example, ammonium sulfate, ammonium phosphate, ammonium nitrate, ureas and vegetable products such as cereals flour, bark meal, wood meal and nutshell meal, cellulose powder and other solid carriers.

The concentrations of active ingredients in the formulations ready for use can vary within wide limits.

They are generally from 0.0001 to 10%, preferably 0.01 to 1%.

The active ingredients may also be used successfully in the ultra low volume (ULV) method which makes it possible to apply formulations containing more than 95% by weight of active ingredient or even the pure active ingredient.

The application rate for the active ingredient in the open is from 0.01 to 3, preferably 0.05 to 1, kg/ha of active substance.

The active ingredients can be mixed with oils of various types, herbicides, fungicides, other pesticides, bactericides, where appropriate just before application (tank mix). These agents can be mixed with the agents according to the invention in the ratio of from 1:10 to 10:1 by weight.

SYNTHESIS EXAMPLES

The methods reported in the following synthesis examples were used to obtain other compounds I by appropriately modifying the starting compounds. The compounds obtained in this way are listed with the physical data in the tables which follow.

1.

N-2-[4-(1,1-Dimethylethoxy)phenoxy]ethoxypyrazole

A solution of 12.7 g (0.15 mol) of N-hydroxypyrazole in 20 ml of DMF was added dropwise to a suspension of 4.95 g (1.1 eq.) of NaH (80% dispersion in mineral oil) in 40 ml of DMF at RT, and the mixture was heated at 70° C. for 1 h. A solution of 40.95 g (0.15 mol) of 2-[4-(1,1-dimethylethoxy)phenoxy]ethyl bromide in 100 ml of DMF was added and the mixture was then heated at 125° C. for 15 h. The solvent was then stripped off in a rotary evaporator, the residue was taken up in ethyl acetate, and the solution was washed twice each with 5% strength NaOH solution and water. Drying and removal of the solvent under reduced pressured resulted in 38.4 g (93%) of the required compound as a pale oil which was employed without further purification in the next stage.

$^1$H-NMR (250 MHz, CDCl$_3$): δ=7.38 (d, 1H); 7.28 (d, 1H); 6.93 (d, 2H); 6.83 (d, 2H); 6.17 (t, 1H); 4.63 (m, 2H); 4.17 (m, 2H); 1.30 (s, 9H) ppm 2. N-2-(4-Hydroxyphenoxy)ethoxypyrazole 9 ml of concentrated hydrochloric acid were added to a solution of 38.4 g (139 mmol) of N-2-[4-(1,1-dimethylethoxy)phenoxy]ethoxypyrazole in 400 ml of ethanol/water (10/1) and the mixture was then refluxed for 8 h. After cooling to RT, the solvent was removed under reduced pressure, the residue was taken up in ethyl acetate, and the solution was washed several times with water. Drying and concentration of the organic phase resulted in 29.6 g (97%) of the required compound as a viscous oil which was employed without further purification in the next stage.

1H-NMR (250 MHz, CDCl3): δ=7.38 (d, 1H); 7.28 (d, 1H); 6.80 (s, 4H); 6.18 (t, 1H); 5.8 (br. s, 1H); 4.62 (m, 2H); 4.12 (m, 2H) ppm

3

1-(3-Cyclopropyl-5-isoxazolylmethoxy)-4-[2-(1-pyrazolyloxy)ethoxy]benzene (compound No. 1.003)

A solution of 2.5 g (11.4 mmol) of N-2-(4-hydroxyphenoxy)ethoxypyrazole in 30 ml of DMF was added dropwise to a suspension of 0.37 g (1.1 eq.) of NaH (80% dispersion in mineral oil) in 20 ml of DMF at RT, and the mixture was heated at 70° C. for 1 h. A solution of 1.8 g (11.4 mmol) of 3-cyclopropyl-5-chloromethylisoxazole in 20 ml of DMF was added and the mixture was heated at 125° C. for 12 h. The solvent was evaporated off, the residue was taken up in ethyl acetate, and the solution was washed three times each with saturated NaHCO: solution and water. Drying, removal of the solvent and purification of the crude product by chromatography (silica gel, cyclohexane/ethyl acetate 1:2) resulted in 2.3 g (60%) of the required hydroquinone diether; melting point 65°-67° C.

4.

1-(2-Methyl-1,3,4-thiadiazol-5-ylmethoxy)-4-[2-(1-pyrazolyloxy)ethoxy]benzene (compound No. 1.009)

A solution of 3.7 g (16.8 mmol) of N-2-(4-hydroxyphenoxy)ethoxypyrazole in 30 ml of DMF was added dropwise to a suspension of 0.55 g (1.1 eq.) of NaH (80% dispersion in mineral oil) in 30 ml of DMF at RT, and the mixture was heated at 70° C. for 1 h. A solution of 2.5 g (16.8 mmol) of 2-methyl-5-chloromethyl-1,3,4-thiadiazole in 20 ml of DMF was added and then the mixture was heated at 120° C. for 8 h. The mixture was cooled to RT and then diluted with ethyl acetate and washed twice each with 5% strength NaOH solution, water and saturated NaCl solution. Removal of the solvent and recrystallization of the resulting solid from hexane/ethyl acetate (4:1) gave 3.1 g (56%) of the required hydroquinone diether; melting point 93°-96° C.

5.

1-(2-Methyl-1,3,4-thiadiazol-5-ylmethoxy)-4-[2-methyl-2-(2-pyridinyloxy)ethoxy]benzene (compound No. 1.021)

A solution of 4.46 g (18.2 mmol) of 4-[2-methyl-2-(2-pyridinyloxy)ethoxy]phenol in 30 ml of DMF was added to a suspension of 0.6 g (1.1 eq.) of NaH (80% dispersion in mineral oil) in 30 ml of DMF at RT and the mixture was then heated at 80° C. for 1 h. A solution of 2.7 g (18.2 mmol) of 2-methyl-5-chloromethyl-1,3,4-thiadiazole in 20 ml of DMF was added and the mixture was then heated at 120° C. for 6 h. The solvent was stripped off in a rotary evaporator, the residue was taken up in ethyl acetate, and the solution was washed three times with water. Drying, removal of the solvent and purification of the crude product by chromatography (silica gel, cyclohexane/ethyl acetate 2:1) resulted in 2.9 g (45%) of colorless crystals; melting point 72°-78° C.

TABLE 1

| No. | X | $A^1$ | $R^1$ | $A^2$ | $R^2$ | Physic. data, m.p. [°C.] 1H-NMR (signal of $A^1$) [ppm] (CDCl3, 250 MHz) |
|---|---|---|---|---|---|---|
| 1.001 | H3C-isoxazole | CH2 | H | CH2CH2 | pyrazole | 82–84 |
| 1.002 | t-Bu-isoxazole | CH2 | H | CH2CH2 | pyrazole | δ = 5.14 |
| 1.003 | cyclopropyl-isoxazole | CH2 | H | CH2CH2 | pyrazole | 65–67 |
| 1.004 | cyclopropyl-isoxazole | CH2 | H | CH2CH2 | Cl-pyrazole | 90–91 |
| 1.005 | Cl,Cl-pyrimidine | CH2 | H | CH2CH2 | pyrazole | 82–88 |
| 1.006 | Cl,Cl-pyrimidine | CH2 | H | CH2CH2 | Cl-pyrazole | 66–72 |

TABLE 1-continued

I

| No. | X | A¹ | R¹ | A² | R² | Physic. data, m.p. [°C.] ¹H-NMR (signal of A¹) [ppm] (CDCl₃, 250 MHz) |
|---|---|---|---|---|---|---|
| 1.007 | (isopropyl-1,3,4-oxadiazole) | CH₂ | H | CH₂CH₂ | (pyrazol-1-yl) | δ = 5.17 |
| 1.008 | (cyclopropyl-1,3,4-oxadiazole) | CH₂ | H | CH₂CH₂ | (pyrazol-1-yl) | 47–48 |
| 1.009 | (methyl-1,3,4-thiadiazole) | CH₂ | H | CH₂CH₂ | (pyrazol-1-yl) | 93–96 |
| 1.010 | (isopropyl-1,3,4-thiadiazole) | CH₂ | H | CH₂CH₂ | (pyrazol-1-yl) | δ = 5.38 |
| 1.011 | (cyclopropyl-1,3,4-thiadiazole) | CH₂ | H | CH₂CH₂ | (pyrazol-1-yl) | 64–65 |
| 1.012 | (ethoxy-1,3,4-thiadiazole) | CH₂ | H | CH₂CH₂ | (pyrazol-1-yl) | δ = 4.98 |
| 1.013 | (cyclopropyl-1,3,4-thiadiazole) | CH₂ | H | CH₂CH₂ | (4-chloropyrazol-1-yl) | 55–59 |
| 1.014 | (3-methylisoxazole) | CH₂ | H | CH₂CH(CH₃) | (pyridin-2-yl) | 68–71 |
| 1.015 | (3-isopropylisoxazole) | CH₂ | H | CH₂CH(CH₃) | (pyridin-2-yl) | δ = 5.02 |
| 1.016 | (3-cyclopropylisoxazole) | CH₂ | H | CH₂CH(CH₃) | (pyridin-2-yl) | 60–72 |
| 1.017 | (4,5-dichloroimidazole) | CH₂ | H | CH₂CH(CH₃) | (pyridin-2-yl) | δ = 5.57 |
| 1.018 | (methyl-1,3,4-oxadiazole) | CH₂ | H | CH₂CH(CH₃) | (pyridin-2-yl) | δ = 5.33 |

TABLE 1-continued

| No. | X | A¹ | R¹ | A² | R² | Physic. data, m.p. [°C] ¹H-NMR (signal of A¹) [ppm] (CDCl₃, 250 MHz) |
|---|---|---|---|---|---|---|
| 1.019 | (N—N, O ring, iPr, •) | $CH_2$ | H | $CH_2CH(CH_3)$ | 2-pyridyl | δ = 5.15 |
| 1.020 | (N—N, O ring, cyclopropyl, •) | $CH_2$ | H | $CH_2CH(CH_3)$ | 2-pyridyl | δ = 5.12 |
| 1.021 | (N—N, S ring, $H_3C$, •) | $CH_2$ | H | $CH_2CH(CH_3)$ | 2-pyridyl | 72–78 |
| 1.022 | (N—N, S ring, iPr, •) | $CH_2$ | H | $CH_2CH(CH_3)$ | 2-pyridyl | δ = 5.39 |
| 1.023 | (N—N, S ring, cyclopropyl, •) | $CH_2$ | H | $CH_2CH(CH_3)$ | 2-pyridyl | δ = 5.33 |
| 1.024 | (N—N, S ring, $CH_3CH_2O$, •) | $CH_2$ | H | $CH_2CH(CH_3)$ | 2-pyridyl | 58–60 |

We claim:

1. A hydroquinone diether of the formula I

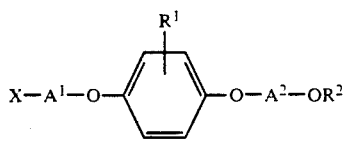

where

A¹ is methylene, ethylene or propylene, each of which can carry one or two $C_1$-$C_3$-alkyl radicals;

A² is ethylene or propylene, each of which can carry one or two $C_1$-$C_3$-alkyl radicals;

R¹ is hydrogen, halogen or $C_1$-$C_8$-alkyl;

R² is pyrazolyl which can carry one to three of the following: halogen or $C_1$-$C_3$ alkyl, X is a member selected from the group of heteroaromatic radicals consisting of furyl, isoxazolyl, oxazoly, 1,2,4-oxadiazolyl, or 1,3,4-oxadiazolyl, where these heteroaromatic radicals can carry one to three of the following: nitro, halogen, $C_1$-$C_6$-alkyl, $C_1$-$C_4$- haloalkyl, $C_1$-$C_6$-alkoxy, $C_1$-$C_4$-haloalkox $C_1$-$C_4$-alkylthio, $C_1$-$C_3$-alkoxy-$C_1$-$C_4$-alkyl, $C_3$-$C_8$-cycloalyl, $C_2$-$C_8$-alkenyl, phenyl, 1-naphthyl, 2-naphthyl, where aromatic radicals in turn may carry one to five halogen atoms and one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio, or where the aromatic radicals in turn may carry one to five halogen atoms or one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio.

2. A pesticide containing an effective amount of a compound of the formula I as claimed in claim 1 and inert additives.

3. A method for controlling pests, which comprises treating the pests and/or their habitat with an effective amount of a compound of the formula I as claimed in claim 1.

4. A compound according to claim 1 wherein X is a member selected from the group of heteroaromatic radicals consisting of isoxazolyl, oxazolyl, 1,2,4-oxadiazolyl or 1,3,4-oxadiazolyl.

* * * * *

UNITED STATES PATENT AND TRADEMARK OFFICE
CERTIFICATE OF CORRECTION

PATENT NO. : 5,221,684

DATED : June 22, 1993

INVENTOR(S) : NUEBLING et al.

It is certified that error appears in the above-identified patent and that said Letters Patent is hereby corrected as shown below:

Claim 1, column 39, line 61, "haloalkox" should be --haloalkoxy--.

Claim 1, column 40, line 39, "$C_3-C_8$-cyloalyl" should read
    --$C_3-C_8$-cycloalkyl--.

Signed and Sealed this

Twenty-ninth Day of March, 1994

Attest:

BRUCE LEHMAN

Attesting Officer     Commissioner of Patents and Trademarks